(12) United States Patent
Wang et al.

(10) Patent No.: US 10,259,119 B2
(45) Date of Patent: Apr. 16, 2019

(54) MULTI-CAMERA MOBILE TELECONFERENCING PLATFORM

(71) Applicants: Yulun Wang, Goleta, CA (US); Charles S. Jordan, Santa Barbara, CA (US); Marco Pinter, Santa Barbara, CA (US); Jonathan Southard, Santa Barbara, CA (US); Keith Phillip Laby, Oakland, CA (US); John Cody Herzog, Santa Barbara, CA (US)

(72) Inventors: Yulun Wang, Goleta, CA (US); Charles S. Jordan, Santa Barbara, CA (US); Marco Pinter, Santa Barbara, CA (US); Jonathan Southard, Santa Barbara, CA (US); Keith Phillip Laby, Oakland, CA (US); John Cody Herzog, Santa Barbara, CA (US)

(73) Assignee: INTOUCH TECHNOLOGIES, INC., Goleta, CA (US)

( * ) Notice: Subject to any disclaimer, the term of this patent is extended or adjusted under 35 U.S.C. 154(b) by 0 days.

(21) Appl. No.: 14/924,453

(22) Filed: Oct. 27, 2015

(65) Prior Publication Data

US 2016/0046024 A1    Feb. 18, 2016

Related U.S. Application Data

(63) Continuation of application No. 11/240,941, filed on Sep. 30, 2005, now Pat. No. 9,198,728.

(51) Int. Cl.
*A61B 34/00*    (2016.01)
*B25J 9/16*    (2006.01)
(Continued)

(52) U.S. Cl.
CPC ............ *B25J 9/1689* (2013.01); *A61B 34/35* (2016.02); *A61B 34/70* (2016.02); *B25J 5/00* (2013.01);
(Continued)

(58) Field of Classification Search
USPC .................................................. 700/245–264
See application file for complete search history.

(56) References Cited

U.S. PATENT DOCUMENTS 3,821,995 A    7/1974 Aghnides
4,107,689 A    8/1978 Jellinek
(Continued)

FOREIGN PATENT DOCUMENTS

AU    1216200 A    5/2000
CA    2289697 A1    11/1998
(Continued)

OTHER PUBLICATIONS

Paulos et al., "Social Tele-Embodiment: Understanding Presence", Autonomous Robots, vol. 11, Issue 1, Kluwer Academic Publishers, Jul. 2001, pp. 87-95.
(Continued)

*Primary Examiner* — Jonathan L Sample

(57) ABSTRACT

A remote controlled robot system that includes a mobile robot and a remote control station. A user can control movement of the robot from the remote control station. The mobile robot includes a camera system that can capture and transmit to the remote station a zoom image and a non-zoom image. The remote control station includes a monitor that displays a robot view field. The robot view field can display the non-zoom image. The zoom image can be displayed in the robot view field by highlighting an area of the non-zoom
(Continued)

field. The remote control station may also store camera locations that allow a user to move the camera system to preset locations.

12 Claims, 7 Drawing Sheets

(51) Int. Cl.

| | |
|---|---|
| *H04N 7/18* | (2006.01) |
| *B25J 5/00* | (2006.01) |
| *B25J 13/00* | (2006.01) |
| *B25J 13/06* | (2006.01) |
| *B25J 19/02* | (2006.01) |
| *A61B 34/35* | (2016.01) |
| *G16H 50/50* | (2018.01) |
| *G06F 19/00* | (2018.01) |
| *A61B 90/00* | (2016.01) |
| *A61B 34/30* | (2016.01) |

(52) U.S. Cl.
CPC .............. *B25J 13/006* (2013.01); *B25J 13/06* (2013.01); *B25J 19/021* (2013.01); *G06F 19/00* (2013.01); *G16H 50/50* (2018.01); *H04N 7/185* (2013.01); *A61B 34/25* (2016.02); *A61B 34/30* (2016.02); *A61B 90/361* (2016.02); *G06F 19/3418* (2013.01)

(56) References Cited

U.S. PATENT DOCUMENTS

| | | | |
|---|---|---|---|
| 4,213,182 A | 7/1980 | Eichelberger et al. | |
| 4,413,693 A | 11/1983 | Derby | |
| 4,471,354 A | 9/1984 | Smith | |
| 4,519,466 A | 5/1985 | Shiraishi | |
| 4,553,309 A | 11/1985 | Hess et al. | |
| 4,572,594 A | 2/1986 | Schwartz | |
| 4,625,274 A | 11/1986 | Schroeder | |
| 4,638,445 A | 1/1987 | Mattaboni | |
| 4,652,204 A | 3/1987 | Arnett | |
| 4,669,168 A | 6/1987 | Tamura et al. | |
| 4,679,152 A | 7/1987 | Perdue | |
| 4,697,278 A | 9/1987 | Fleischer | |
| 4,697,472 A | 10/1987 | Hiyane | |
| 4,709,265 A | 11/1987 | Silverman et al. | |
| 4,733,737 A | 3/1988 | Falamak | |
| 4,751,658 A | 6/1988 | Kadonoff et al. | |
| 4,766,581 A | 8/1988 | Korn et al. | |
| 4,777,416 A | 10/1988 | George et al. | |
| 4,797,557 A | 1/1989 | Ohman | |
| 4,803,625 A | 2/1989 | Fu et al. | |
| 4,847,764 A | 7/1989 | Halvorson | |
| 4,875,172 A | 10/1989 | Kanayama | |
| 4,878,501 A | 11/1989 | Shue | |
| 4,942,512 A | 7/1990 | Kohno | |
| 4,942,538 A | 7/1990 | Yuan et al. | |
| 4,953,159 A | 8/1990 | Hayden et al. | |
| 4,974,607 A | 12/1990 | Miwa | |
| 4,977,971 A | 12/1990 | Crane et al. | |
| 5,006,988 A | 4/1991 | Borenstein et al. | |
| 5,040,116 A | 8/1991 | Evans et al. | |
| 5,051,906 A | 9/1991 | Evans et al. | |
| 5,073,749 A | 12/1991 | Kanayama | |
| 5,084,828 A | 1/1992 | Kaufman et al. | |
| 5,130,794 A | 7/1992 | Ritchey | |
| 5,148,591 A | 9/1992 | Pryor | |
| 5,153,833 A | 10/1992 | Gordon et al. | |
| 5,155,684 A | 10/1992 | Burke et al. | |
| 5,157,491 A | 10/1992 | Kassatly | |
| 5,182,641 A | 1/1993 | Diner et al. | |
| 5,186,270 A | 2/1993 | West | |
| 5,193,143 A | 3/1993 | Kaemmerer et al. | |
| 5,217,453 A | 6/1993 | Wilk | |
| 5,220,263 A | 6/1993 | Onishi et al. | |
| 5,224,157 A | 6/1993 | Yamada et al. | |
| 5,230,023 A | 7/1993 | Nakano | |
| 5,231,693 A | 7/1993 | Backes et al. | |
| 5,236,432 A | 8/1993 | Matsen et al. | |
| 5,262,944 A | 11/1993 | Weisner et al. | |
| 5,305,427 A | 4/1994 | Nagata | |
| 5,315,287 A | 5/1994 | Sol | |
| 5,319,443 A * | 6/1994 | Watanabe | B25J 9/1692 356/614 |
| 5,319,611 A | 6/1994 | Korba | |
| 5,341,242 A | 8/1994 | Gilboa et al. | |
| 5,341,459 A | 8/1994 | Backes | |
| 5,341,854 A | 8/1994 | Zezulka et al. | |
| 5,347,306 A | 9/1994 | Nitta | |
| 5,347,457 A | 9/1994 | Tanaka et al. | |
| 5,350,033 A | 9/1994 | Kraft | |
| 5,366,896 A | 11/1994 | Margrey et al. | |
| 5,374,879 A | 12/1994 | Pin et al. | |
| 5,375,195 A | 12/1994 | Johnston | |
| 5,400,068 A | 3/1995 | Ishida et al. | |
| 5,412,400 A * | 5/1995 | Takahara | G05B 23/0272 715/788 |
| 5,417,210 A | 5/1995 | Funda et al. | |
| 5,419,008 A | 5/1995 | West | |
| 5,436,542 A | 7/1995 | Petelin et al. | |
| 5,441,042 A | 8/1995 | Putman | |
| 5,441,047 A | 8/1995 | David et al. | |
| 5,442,728 A | 8/1995 | Kaufman et al. | |
| 5,462,051 A | 10/1995 | Oka et al. | |
| 5,486,853 A | 1/1996 | Baxter et al. | |
| 5,510,832 A | 4/1996 | Garcia | |
| 5,511,147 A | 4/1996 | Abdel-Malek | |
| 5,528,289 A | 6/1996 | Cortjens et al. | |
| 5,539,741 A | 7/1996 | Barraclough et al. | |
| 5,544,649 A | 8/1996 | David et al. | |
| 5,550,577 A | 8/1996 | Verbiest et al. | |
| 5,553,609 A | 9/1996 | Chen et al. | |
| 5,563,998 A | 10/1996 | Yaksich et al. | |
| 5,572,229 A | 11/1996 | Fisher | |
| 5,572,999 A | 11/1996 | Funda et al. | |
| 5,594,859 A | 1/1997 | Palmer et al. | |
| 5,600,573 A | 2/1997 | Hendricks et al. | |
| 5,617,539 A | 4/1997 | Ludwig et al. | |
| 5,619,341 A | 4/1997 | Auyeung et al. | |
| 5,623,679 A | 4/1997 | Rivette et al. | |
| 5,630,566 A | 5/1997 | Case | |
| 5,636,218 A | 6/1997 | Ishikawa et al. | |
| 5,652,849 A | 7/1997 | Conway et al. | |
| 5,657,246 A | 8/1997 | Hogan et al. | |
| 5,659,779 A | 8/1997 | Laird et al. | |
| 5,673,082 A | 9/1997 | Wells et al. | |
| 5,675,229 A | 10/1997 | Thorne | |
| 5,682,199 A | 10/1997 | Lankford | |
| 5,684,695 A | 11/1997 | Bauer | |
| 5,701,904 A | 12/1997 | Simmons et al. | |
| 5,734,805 A | 3/1998 | Isensee et al. | |
| 5,739,657 A | 4/1998 | Takayama et al. | |
| 5,748,629 A | 5/1998 | Caldara et al. | |
| 5,749,058 A | 5/1998 | Hashimoto | |
| 5,749,362 A | 5/1998 | Funda et al. | |
| 5,754,631 A | 5/1998 | Cave | |
| 5,758,079 A | 5/1998 | Ludwig et al. | |
| 5,762,458 A | 6/1998 | Wang et al. | |
| 5,764,731 A | 6/1998 | Yablon | |
| 5,767,897 A | 6/1998 | Howell | |
| 5,786,846 A | 7/1998 | Hiroaki | |
| 5,787,545 A | 8/1998 | Colens | |
| 5,793,365 A | 8/1998 | Tang et al. | |
| 5,801,755 A | 9/1998 | Echerer | |
| 5,802,494 A | 9/1998 | Kuno | |
| 5,836,872 A | 11/1998 | Kenet et al. | |
| 5,838,575 A | 11/1998 | Lion | |
| 5,844,599 A | 12/1998 | Hildin | |
| 5,857,534 A | 1/1999 | Devault et al. | |
| 5,867,494 A | 2/1999 | Krishnaswamy et al. | |
| 5,867,653 A | 2/1999 | Aras et al. | |
| 5,871,451 A | 2/1999 | Unger et al. | |

(56) References Cited

U.S. PATENT DOCUMENTS

| | | | |
|---|---|---|---|
| 5,872,922 A * | 2/1999 | Hogan | H04N 7/142 348/14.03 |
| 5,876,325 A | 3/1999 | Mizuno et al. | |
| 5,911,036 A | 6/1999 | Wright et al. | |
| 5,917,958 A | 6/1999 | Nunally et al. | |
| 5,927,423 A | 7/1999 | Wada et al. | |
| 5,949,758 A | 9/1999 | Kober | |
| 5,954,692 A | 9/1999 | Smith et al. | |
| 5,959,423 A | 9/1999 | Nakanishi et al. | |
| 5,961,446 A | 10/1999 | Beller et al. | |
| 5,966,130 A | 10/1999 | Benman, Jr. | |
| 5,973,724 A | 10/1999 | Riddle | |
| 5,974,446 A | 10/1999 | Sonnenreich et al. | |
| 5,983,263 A | 11/1999 | Rothrock et al. | |
| 5,995,119 A | 11/1999 | Cosatto et al. | |
| 5,995,884 A | 11/1999 | Allen et al. | |
| 5,999,977 A | 12/1999 | Riddle | |
| 6,006,946 A | 12/1999 | Williams et al. | |
| 6,031,845 A | 2/2000 | Walding | |
| 6,036,812 A | 3/2000 | Williams et al. | |
| 6,047,259 A | 4/2000 | Campbell et al. | |
| 6,091,219 A | 7/2000 | Maruo et al. | |
| 6,113,343 A | 9/2000 | Goldenberg et al. | |
| 6,133,944 A * | 10/2000 | Braun | H04N 5/232 348/39 |
| 6,135,228 A | 10/2000 | Asada et al. | |
| 6,148,100 A | 11/2000 | Anderson et al. | |
| 6,160,582 A | 12/2000 | Hill | |
| 6,170,929 B1 | 1/2001 | Wilson et al. | |
| 6,175,779 B1 | 1/2001 | Barrett | |
| 6,189,034 B1 | 2/2001 | Riddle | |
| 6,201,984 B1 | 3/2001 | Funda et al. | |
| 6,211,903 B1 | 4/2001 | Bullister | |
| 6,219,587 B1 | 4/2001 | Ahlin et al. | |
| 6,232,735 B1 * | 5/2001 | Baba | B25J 9/1689 318/567 |
| 6,233,504 B1 | 5/2001 | Das et al. | |
| 6,233,735 B1 | 5/2001 | Ebihara | |
| 6,250,928 B1 | 6/2001 | Poggio et al. | |
| 6,256,556 B1 | 7/2001 | Zenke | |
| 6,259,806 B1 | 7/2001 | Green | |
| 6,259,956 B1 | 7/2001 | Myers et al. | |
| 6,266,162 B1 | 7/2001 | Okamura et al. | |
| 6,266,577 B1 | 7/2001 | Popp et al. | |
| 6,289,263 B1 | 9/2001 | Mukherjee | |
| 6,292,713 B1 | 9/2001 | Jouppi et al. | |
| 6,292,714 B1 | 9/2001 | Okabayashi | |
| 6,304,050 B1 | 10/2001 | Skaar et al. | |
| 6,314,631 B1 | 11/2001 | Pryor | |
| 6,317,652 B1 | 11/2001 | Osada | |
| 6,317,953 B1 | 11/2001 | Pryor | |
| 6,321,137 B1 | 11/2001 | De Smet | |
| 6,324,184 B1 | 11/2001 | Hou et al. | |
| 6,324,443 B1 | 11/2001 | Kurakake et al. | |
| 6,325,756 B1 | 12/2001 | Webb et al. | |
| 6,327,516 B1 | 12/2001 | Zenke | |
| 6,330,486 B1 | 12/2001 | Padula | |
| 6,330,493 B1 | 12/2001 | Takahashi et al. | |
| 6,346,950 B1 | 2/2002 | Jouppi | |
| 6,346,962 B1 | 2/2002 | Goodridge | |
| 6,369,847 B1 | 4/2002 | James et al. | |
| 6,373,855 B1 | 4/2002 | Downing et al. | |
| 6,381,515 B1 | 4/2002 | Inoue et al. | |
| 6,389,329 B1 | 5/2002 | Colens | |
| 6,400,378 B1 | 6/2002 | Snook | |
| 6,408,230 B2 | 6/2002 | Wada | |
| 6,411,055 B1 | 6/2002 | Fujita et al. | |
| 6,430,471 B1 | 8/2002 | Kintou et al. | |
| 6,430,475 B2 | 8/2002 | Okamoto et al. | |
| 6,438,457 B1 | 8/2002 | Yokoo et al. | |
| 6,445,964 B1 | 9/2002 | White et al. | |
| 6,449,762 B1 | 9/2002 | Mcelvain | |
| 6,452,915 B1 | 9/2002 | Jorgensen | |
| 6,457,043 B1 | 9/2002 | Kwak et al. | |
| 6,459,955 B1 | 10/2002 | Bartsch et al. | |
| 6,463,352 B1 | 10/2002 | Tadokoro et al. | |
| 6,463,361 B1 | 10/2002 | Wang et al. | |
| 6,466,844 B1 | 10/2002 | Ikeda et al. | |
| 6,468,265 B1 | 10/2002 | Evans et al. | |
| 6,470,235 B2 | 10/2002 | Kasuga et al. | |
| 6,474,434 B1 | 11/2002 | Bech | |
| 6,480,762 B1 | 11/2002 | Uchikubo et al. | |
| 6,491,701 B2 | 12/2002 | Tierney et al. | |
| 6,496,099 B2 | 12/2002 | Wang et al. | |
| 6,496,755 B2 | 12/2002 | Wallach et al. | |
| 6,501,740 B1 | 12/2002 | Sun et al. | |
| 6,507,773 B2 | 1/2003 | Parker et al. | |
| 6,522,906 B1 | 2/2003 | Salisbury et al. | |
| 6,523,629 B1 | 2/2003 | Buttz et al. | |
| 6,526,332 B2 | 2/2003 | Sakamoto et al. | |
| 6,529,620 B2 | 3/2003 | Thompson | |
| 6,529,765 B1 | 3/2003 | Franck et al. | |
| 6,529,802 B1 | 3/2003 | Kawakita et al. | |
| 6,532,404 B2 | 3/2003 | Colens | |
| 6,535,182 B2 | 3/2003 | Stanton | |
| 6,535,793 B2 * | 3/2003 | Allard | B25J 9/1689 318/628 |
| 6,540,039 B1 | 4/2003 | Yu et al. | |
| 6,543,899 B2 | 4/2003 | Covannon et al. | |
| 6,549,215 B2 * | 4/2003 | Jouppi | G05D 1/0246 345/660 |
| 6,563,533 B1 | 5/2003 | Colby | |
| 6,567,038 B1 | 5/2003 | Granot et al. | |
| 6,580,246 B2 | 6/2003 | Jacobs | |
| 6,581,798 B2 | 6/2003 | Liff et al. | |
| 6,584,376 B1 | 6/2003 | Van Kommer | |
| 6,587,750 B2 | 7/2003 | Gerbi et al. | |
| 6,590,604 B1 | 7/2003 | Tucker et al. | |
| 6,594,269 B1 | 7/2003 | Polcyn | |
| 6,594,552 B1 | 7/2003 | Nowlin et al. | |
| 6,597,392 B1 | 7/2003 | Jenkins et al. | |
| 6,602,469 B1 | 8/2003 | Maus et al. | |
| 6,604,019 B2 | 8/2003 | Ahlin et al. | |
| 6,604,021 B2 | 8/2003 | Imai et al. | |
| 6,611,120 B2 | 8/2003 | Song et al. | |
| 6,643,496 B1 | 11/2003 | Shimoyama et al. | |
| 6,646,677 B2 | 11/2003 | Noro et al. | |
| 6,650,748 B1 | 11/2003 | Edwards et al. | |
| 6,666,374 B1 | 12/2003 | Green et al. | |
| 6,667,592 B2 | 12/2003 | Jacobs et al. | |
| 6,674,259 B1 | 1/2004 | Norman et al. | |
| 6,684,129 B2 | 1/2004 | Salisbury et al. | |
| 6,691,000 B2 | 2/2004 | Nagai et al. | |
| 6,693,585 B1 | 2/2004 | Macleod | |
| 6,710,797 B1 | 3/2004 | Mcnelley et al. | |
| 6,724,823 B2 | 4/2004 | Rovati et al. | |
| 6,728,599 B2 | 4/2004 | Wang et al. | |
| 6,763,282 B2 | 7/2004 | Glenn et al. | |
| 6,763,284 B2 * | 7/2004 | Watanabe | B25J 9/1697 219/121.67 |
| 6,764,373 B1 | 7/2004 | Osawa et al. | |
| 6,769,771 B2 | 8/2004 | Trumbull | |
| 6,781,606 B2 | 8/2004 | Jouppi | |
| 6,784,916 B2 | 8/2004 | Smith | |
| 6,785,589 B2 | 8/2004 | Eggenberger et al. | |
| 6,791,550 B2 | 9/2004 | Goldhor et al. | |
| 6,798,753 B1 | 9/2004 | Doganata et al. | |
| 6,799,065 B1 | 9/2004 | Niemeyer | |
| 6,799,088 B2 | 9/2004 | Wang et al. | |
| 6,804,580 B1 | 10/2004 | Stoddard et al. | |
| 6,804,656 B1 | 10/2004 | Rosenfeld et al. | |
| 6,810,411 B1 | 10/2004 | Coughlin et al. | |
| 6,816,192 B1 | 11/2004 | Nishikawa | |
| 6,816,754 B2 | 11/2004 | Mukai et al. | |
| 6,836,703 B2 | 12/2004 | Wang et al. | |
| 6,839,612 B2 | 1/2005 | Sanchez et al. | |
| 6,840,904 B2 | 1/2005 | Goldberg | |
| 6,845,297 B2 * | 1/2005 | Allard | B25J 9/1689 318/628 |
| 6,852,107 B2 | 2/2005 | Wang et al. | |
| 6,853,878 B2 | 2/2005 | Hirayama et al. | |
| 6,853,880 B2 | 2/2005 | Sakagami et al. | |
| 6,871,117 B2 | 3/2005 | Wang et al. | |
| 6,879,879 B2 | 4/2005 | Jouppi et al. | |

(56) References Cited

U.S. PATENT DOCUMENTS

| | | | |
|---|---|---|---|
| 6,888,333 B2 | 5/2005 | Laby | |
| 6,892,112 B2 | 5/2005 | Wang et al. | |
| 6,893,267 B1 | 5/2005 | Yueh | |
| 6,895,305 B2 | 5/2005 | Lathan et al. | |
| 6,898,484 B2 | 5/2005 | Lemelson et al. | |
| 6,914,622 B1* | 7/2005 | Smith | A47B 21/0073 348/14.05 |
| 6,925,357 B2 | 8/2005 | Wang et al. | |
| 6,951,535 B2 | 10/2005 | Ghodoussi et al. | |
| 6,952,470 B1 | 10/2005 | Tioe et al. | |
| 6,957,712 B2 | 10/2005 | Song et al. | |
| 6,958,706 B2 | 10/2005 | Chaco et al. | |
| 6,965,394 B2 | 11/2005 | Gutta et al. | |
| 6,990,112 B1 | 1/2006 | Brent et al. | |
| 6,995,664 B1* | 2/2006 | Darling | G08B 19/00 340/10.1 |
| 7,007,235 B1 | 2/2006 | Hussein et al. | |
| 7,011,538 B2 | 3/2006 | Chang | |
| 7,015,934 B2 | 3/2006 | Toyama et al. | |
| RE39,080 E | 4/2006 | Johnston | |
| 7,030,757 B2 | 4/2006 | Matsuhira et al. | |
| 7,053,578 B2 | 5/2006 | Diehl et al. | |
| 7,055,210 B2 | 6/2006 | Keppler et al. | |
| 7,058,689 B2 | 6/2006 | Parker et al. | |
| 7,092,001 B2 | 8/2006 | Schulz | |
| 7,096,090 B1* | 8/2006 | Zweig | G05D 1/0022 700/245 |
| 7,115,102 B2 | 10/2006 | Abbruscato | |
| 7,117,067 B2 | 10/2006 | Mclurkin et al. | |
| 7,123,285 B2* | 10/2006 | Smith | A47B 21/0073 348/14.05 |
| 7,123,974 B1 | 10/2006 | Hamilton | |
| 7,123,991 B2 | 10/2006 | Graf et al. | |
| 7,127,325 B2 | 10/2006 | Nagata et al. | |
| 7,129,970 B2 | 10/2006 | James et al. | |
| 7,133,062 B2 | 11/2006 | Castles et al. | |
| 7,142,945 B2 | 11/2006 | Wang et al. | |
| 7,142,947 B2 | 11/2006 | Wang et al. | |
| 7,151,848 B1* | 12/2006 | Watanabe | B25J 9/1656 382/141 |
| 7,151,982 B2 | 12/2006 | Liff et al. | |
| 7,154,526 B2* | 12/2006 | Foote | H04N 7/142 348/14.08 |
| 7,155,306 B2 | 12/2006 | Haitin et al. | |
| 7,156,809 B2 | 1/2007 | Quy | |
| 7,158,859 B2 | 1/2007 | Wang et al. | |
| 7,158,860 B2 | 1/2007 | Wang et al. | |
| 7,158,861 B2 | 1/2007 | Wang et al. | |
| 7,161,322 B2 | 1/2007 | Wang et al. | |
| 7,162,338 B2 | 1/2007 | Goncalves et al. | |
| 7,164,969 B2 | 1/2007 | Wang et al. | |
| 7,164,970 B2 | 1/2007 | Wang et al. | |
| 7,167,448 B2 | 1/2007 | Wookey et al. | |
| 7,171,286 B2* | 1/2007 | Wang | G06F 19/3418 700/248 |
| 7,174,238 B1* | 2/2007 | Zweig | G05D 1/0038 700/245 |
| 7,181,455 B2 | 2/2007 | Wookey et al. | |
| 7,184,559 B2 | 2/2007 | Jouppi | |
| 7,188,000 B2 | 3/2007 | Chiappetta et al. | |
| 7,199,790 B2 | 4/2007 | Rosenberg et al. | |
| 7,202,851 B2 | 4/2007 | Cunningham et al. | |
| 7,206,627 B2 | 4/2007 | Abovitz et al. | |
| 7,215,786 B2 | 5/2007 | Nakadai et al. | |
| 7,219,364 B2 | 5/2007 | Bolle et al. | |
| 7,222,000 B2 | 5/2007 | Wang et al. | |
| 7,227,334 B2 | 6/2007 | Yang et al. | |
| 7,256,708 B2 | 8/2007 | Rosenfeld et al. | |
| 7,262,573 B2 | 8/2007 | Wang et al. | |
| 7,283,153 B2 | 10/2007 | Provost et al. | |
| 7,289,883 B2 | 10/2007 | Wang et al. | |
| 7,292,257 B2 | 11/2007 | Kang et al. | |
| 7,292,912 B2 | 11/2007 | Wang et al. | |
| 7,305,114 B2 | 12/2007 | Wolff et al. | |
| 7,317,685 B1 | 1/2008 | Flott et al. | |
| 7,321,807 B2 | 1/2008 | Laski | |
| 7,332,890 B2 | 2/2008 | Cohen et al. | |
| 7,333,642 B2 | 2/2008 | Green | |
| 7,346,429 B2 | 3/2008 | Goldenberg et al. | |
| 7,352,153 B2 | 4/2008 | Yan | |
| 7,363,121 B1 | 4/2008 | Chen et al. | |
| 7,382,399 B1 | 6/2008 | Mccall et al. | |
| 7,386,730 B2 | 6/2008 | Uchikubo | |
| 7,391,432 B2 | 6/2008 | Terada | |
| 7,400,578 B2 | 7/2008 | Guthrie et al. | |
| 7,404,140 B2 | 7/2008 | ORourke | |
| 7,421,470 B2 | 9/2008 | Ludwig et al. | |
| 7,430,209 B2 | 9/2008 | Porter | |
| 7,432,949 B2 | 10/2008 | Remy et al. | |
| 7,433,921 B2 | 10/2008 | Ludwig et al. | |
| 7,441,953 B2 | 10/2008 | Banks | |
| 7,467,211 B1 | 12/2008 | Herman et al. | |
| 7,483,867 B2 | 1/2009 | Ansari et al. | |
| 7,492,731 B2 | 2/2009 | Hagendorf | |
| 7,510,428 B2 | 3/2009 | Obata et al. | |
| 7,523,069 B1 | 4/2009 | Friedl et al. | |
| 7,525,281 B2 | 4/2009 | Koyanagi et al. | |
| 7,535,486 B2 | 5/2009 | Motomura et al. | |
| 7,557,758 B2 | 7/2009 | Rofougaran | |
| 7,587,260 B2 | 9/2009 | Bruemmer et al. | |
| 7,587,512 B2 | 9/2009 | Ta et al. | |
| 7,590,060 B2 | 9/2009 | Miceli | |
| 7,593,030 B2 | 9/2009 | Wang et al. | |
| 7,599,290 B2 | 10/2009 | Dos Remedios et al. | |
| 7,624,166 B2 | 11/2009 | Foote et al. | |
| 7,630,314 B2 | 12/2009 | Dos Remedios et al. | |
| 7,631,833 B1 | 12/2009 | Ghaleb et al. | |
| 7,643,051 B2 | 1/2010 | Sandberg et al. | |
| 7,647,320 B2 | 1/2010 | Mok et al. | |
| 7,657,560 B1* | 2/2010 | DiRienzo | G06F 19/321 707/600 |
| 7,680,038 B1 | 3/2010 | Gourlay | |
| 7,693,757 B2 | 4/2010 | Zimmerman | |
| 7,698,432 B2 | 4/2010 | Short et al. | |
| 7,703,113 B2 | 4/2010 | Dawson | |
| 7,719,229 B2 | 5/2010 | Kaneko et al. | |
| 7,737,993 B2* | 6/2010 | Kaasila | G06F 3/0481 345/467 |
| 7,739,383 B1 | 6/2010 | Short et al. | |
| 7,756,614 B2 | 7/2010 | Jouppi | |
| 7,761,185 B2 | 7/2010 | Wang et al. | |
| 7,769,492 B2 | 8/2010 | Wang et al. | |
| 7,769,705 B1 | 8/2010 | Luechtefeld | |
| 7,774,158 B2 | 8/2010 | Domingues Goncalves et al. | |
| 7,813,836 B2 | 10/2010 | Wang et al. | |
| 7,831,575 B2 | 11/2010 | Trossell et al. | |
| 7,835,775 B2 | 11/2010 | Sawayama et al. | |
| 7,860,680 B2 | 12/2010 | Arms et al. | |
| 7,861,366 B2 | 1/2011 | Hahm et al. | |
| 7,885,822 B2 | 2/2011 | Akers et al. | |
| 7,890,382 B2 | 2/2011 | Robb et al. | |
| 7,912,583 B2 | 3/2011 | Gutmann et al. | |
| RE42,288 E | 4/2011 | Degioanni | |
| 7,924,323 B2 | 4/2011 | Walker et al. | |
| 7,949,616 B2 | 5/2011 | Levy et al. | |
| 7,956,894 B2 | 6/2011 | Akers et al. | |
| 7,957,837 B2 | 6/2011 | Ziegler et al. | |
| 7,982,763 B2 | 7/2011 | King | |
| 7,982,769 B2 | 7/2011 | Jenkins et al. | |
| 7,987,069 B2 | 7/2011 | Rodgers et al. | |
| 7,995,652 B2* | 8/2011 | Washington | H04N 5/77 348/14.12 |
| 8,077,963 B2 | 12/2011 | Wang et al. | |
| 8,116,910 B2 | 2/2012 | Walters et al. | |
| 8,126,960 B2 | 2/2012 | Obradovich et al. | |
| 8,170,241 B2 | 5/2012 | Roe et al. | |
| 8,179,418 B2 | 5/2012 | Wright et al. | |
| 8,180,486 B2 | 5/2012 | Saito et al. | |
| 8,209,051 B2 | 6/2012 | Wang et al. | |
| 8,212,533 B2 | 7/2012 | Ota | |
| 8,265,793 B2 | 9/2012 | Cross et al. | |
| 8,287,522 B2 | 10/2012 | Moses et al. | |
| 8,292,807 B2 | 10/2012 | Perkins et al. | |

(56) References Cited

U.S. PATENT DOCUMENTS

| | | | |
|---|---|---|---|
| 8,320,534 B2 | 11/2012 | Kim et al. | |
| 8,340,654 B2 | 12/2012 | Bratton et al. | |
| 8,340,819 B2 | 12/2012 | Mangaser et al. | |
| 8,348,675 B2 | 1/2013 | Dohrmann | |
| 8,374,171 B2 | 2/2013 | Cho et al. | |
| 8,400,491 B1 | 3/2013 | Panpaliya et al. | |
| 8,401,275 B2 | 3/2013 | Wang et al. | |
| 8,423,284 B2 | 4/2013 | O Shea | |
| 8,451,731 B1 | 5/2013 | Lee et al. | |
| 8,463,435 B2 | 6/2013 | Herzog et al. | |
| 8,503,340 B1 | 8/2013 | Xu | |
| 8,515,577 B2 | 8/2013 | Wang et al. | |
| 8,527,094 B2 | 9/2013 | Kumar et al. | |
| 8,532,860 B2 | 9/2013 | Daly | |
| 8,610,786 B2 | 12/2013 | Ortiz | |
| 8,612,051 B2 | 12/2013 | Norman et al. | |
| 8,639,797 B1 | 1/2014 | Pan et al. | |
| 8,670,017 B2 | 3/2014 | Stuart et al. | |
| 8,726,454 B2 | 5/2014 | Gilbert et al. | |
| 8,836,751 B2 | 9/2014 | Ballantyne et al. | |
| 8,849,679 B2 | 9/2014 | Wang et al. | |
| 8,849,680 B2 | 9/2014 | Wright et al. | |
| 8,861,750 B2 | 10/2014 | Roe et al. | |
| 8,897,920 B2 | 11/2014 | Wang et al. | |
| 8,902,278 B2 | 12/2014 | Pinter et al. | |
| 2001/0002448 A1 | 5/2001 | Wilson et al. | |
| 2001/0010053 A1 | 7/2001 | Ben-Shachar et al. | |
| 2001/0020200 A1 | 9/2001 | Das et al. | |
| 2001/0034475 A1 | 10/2001 | Flach et al. | |
| 2001/0034544 A1 | 10/2001 | Mo | |
| 2001/0037163 A1 | 11/2001 | Allard | |
| 2001/0048464 A1 | 12/2001 | Barnett | |
| 2001/0051881 A1 | 12/2001 | Filler | |
| 2001/0054071 A1 | 12/2001 | Loeb | |
| 2001/0055373 A1 | 12/2001 | Yamashita | |
| 2002/0015296 A1 | 2/2002 | Howell et al. | |
| 2002/0027597 A1 | 3/2002 | Sachau | |
| 2002/0027652 A1 | 3/2002 | Paromtchik et al. | |
| 2002/0033880 A1 | 3/2002 | Sul et al. | |
| 2002/0038168 A1 | 3/2002 | Kasuga et al. | |
| 2002/0044201 A1 | 4/2002 | Alexander et al. | |
| 2002/0049517 A1 | 4/2002 | Ruffner | |
| 2002/0055917 A1 | 5/2002 | Muraca | |
| 2002/0057279 A1 | 5/2002 | Jouppi | |
| 2002/0058929 A1 | 5/2002 | Green | |
| 2002/0059587 A1 | 5/2002 | Cofano et al. | |
| 2002/0063726 A1 | 5/2002 | Jouppi | |
| 2002/0073429 A1 | 6/2002 | Beane et al. | |
| 2002/0082498 A1 | 6/2002 | Wendt et al. | |
| 2002/0085030 A1 | 7/2002 | Ghani | |
| 2002/0095238 A1 | 7/2002 | Ahlin et al. | |
| 2002/0095239 A1 | 7/2002 | Wallach et al. | |
| 2002/0098879 A1 | 7/2002 | Rheey | |
| 2002/0104094 A1 | 8/2002 | Alexander et al. | |
| 2002/0106998 A1 | 8/2002 | Presley et al. | |
| 2002/0109770 A1 | 8/2002 | Terada | |
| 2002/0109775 A1 | 8/2002 | White et al. | |
| 2002/0111988 A1 | 8/2002 | Sato | |
| 2002/0120362 A1 | 8/2002 | Lathan | |
| 2002/0128985 A1 | 9/2002 | Greenwald | |
| 2002/0130950 A1 | 9/2002 | James et al. | |
| 2002/0133062 A1 | 9/2002 | Arling et al. | |
| 2002/0141595 A1 | 10/2002 | Alexander | |
| 2002/0143923 A1 | 10/2002 | Alexander | |
| 2002/0173877 A1* | 11/2002 | Zweig | B25J 9/1689 700/245 |
| 2002/0177925 A1 | 11/2002 | Onishi et al. | |
| 2002/0183894 A1 | 12/2002 | Wang et al. | |
| 2002/0184674 A1 | 12/2002 | Xi et al. | |
| 2002/0186243 A1 | 12/2002 | Ellis et al. | |
| 2003/0021107 A1 | 1/2003 | Howell et al. | |
| 2003/0030397 A1 | 2/2003 | Simmons | |
| 2003/0048481 A1 | 3/2003 | Kobayashi et al. | |
| 2003/0050733 A1 | 3/2003 | Wang et al. | |
| 2003/0050734 A1 | 3/2003 | Lapham | |
| 2003/0060808 A1 | 3/2003 | Wilk | |
| 2003/0063600 A1 | 4/2003 | Noma et al. | |
| 2003/0069752 A1 | 4/2003 | Ledain et al. | |
| 2003/0080901 A1 | 5/2003 | Piotrowski | |
| 2003/0100892 A1 | 5/2003 | Morley et al. | |
| 2003/0104806 A1 | 6/2003 | Ruef et al. | |
| 2003/0112823 A1 | 6/2003 | Collins et al. | |
| 2003/0114962 A1 | 6/2003 | Niemeyer et al. | |
| 2003/0120714 A1 | 6/2003 | Wolff et al. | |
| 2003/0126361 A1 | 7/2003 | Slater et al. | |
| 2003/0135097 A1 | 7/2003 | Wiederhold et al. | |
| 2003/0135203 A1 | 7/2003 | Wang et al. | |
| 2003/0144579 A1 | 7/2003 | Buss | |
| 2003/0144649 A1 | 7/2003 | Ghodoussi et al. | |
| 2003/0151658 A1 | 8/2003 | Smith | |
| 2003/0152145 A1 | 8/2003 | Kawakita | |
| 2003/0171710 A1 | 9/2003 | Bassuk et al. | |
| 2003/0174285 A1 | 9/2003 | Trumbull | |
| 2003/0180697 A1 | 9/2003 | Kim et al. | |
| 2003/0195662 A1 | 10/2003 | Wang et al. | |
| 2003/0199000 A1 | 10/2003 | Valkirs et al. | |
| 2003/0206242 A1 | 11/2003 | Choi | |
| 2003/0212472 A1 | 11/2003 | Mckee | |
| 2003/0216833 A1 | 11/2003 | Mukai et al. | |
| 2003/0216834 A1* | 11/2003 | Allard | B25J 9/1689 700/245 |
| 2003/0220541 A1 | 11/2003 | Salisbury et al. | |
| 2003/0220715 A1 | 11/2003 | Kneifel et al. | |
| 2003/0231244 A1 | 12/2003 | Bonilla et al. | |
| 2003/0232649 A1 | 12/2003 | Gizis et al. | |
| 2003/0236590 A1 | 12/2003 | Park et al. | |
| 2004/0001197 A1 | 1/2004 | Ko et al. | |
| 2004/0001676 A1 | 1/2004 | Colgan et al. | |
| 2004/0008138 A1 | 1/2004 | Hockley, Jr. et al. | |
| 2004/0010344 A1 | 1/2004 | Hiratsuka et al. | |
| 2004/0012362 A1 | 1/2004 | Tsurumi | |
| 2004/0013295 A1 | 1/2004 | Sabe et al. | |
| 2004/0017475 A1 | 1/2004 | Akers et al. | |
| 2004/0019406 A1 | 1/2004 | Wang et al. | |
| 2004/0024490 A1 | 2/2004 | Mclurkin et al. | |
| 2004/0041904 A1 | 3/2004 | Lapalme et al. | |
| 2004/0065073 A1 | 4/2004 | Nash | |
| 2004/0068657 A1 | 4/2004 | Alexander et al. | |
| 2004/0078219 A1 | 4/2004 | Kaylor et al. | |
| 2004/0080610 A1 | 4/2004 | James et al. | |
| 2004/0088077 A1 | 5/2004 | Jouppi et al. | |
| 2004/0088078 A1 | 5/2004 | Jouppi et al. | |
| 2004/0093219 A1* | 5/2004 | Shin | B25J 9/0003 704/275 |
| 2004/0093409 A1 | 5/2004 | Thompson et al. | |
| 2004/0095516 A1 | 5/2004 | Rohlicek | |
| 2004/0098167 A1 | 5/2004 | Yi et al. | |
| 2004/0102167 A1 | 5/2004 | Shim et al. | |
| 2004/0107254 A1 | 6/2004 | Ludwig et al. | |
| 2004/0107255 A1 | 6/2004 | Ludwig et al. | |
| 2004/0117065 A1 | 6/2004 | Wang et al. | |
| 2004/0117067 A1 | 6/2004 | Jouppi | |
| 2004/0123158 A1 | 6/2004 | Roskind | |
| 2004/0135879 A1 | 7/2004 | Stacy et al. | |
| 2004/0138547 A1 | 7/2004 | Wang et al. | |
| 2004/0143421 A1 | 7/2004 | Wang et al. | |
| 2004/0148638 A1 | 7/2004 | Weisman et al. | |
| 2004/0150725 A1 | 8/2004 | Taguchi | |
| 2004/0153211 A1 | 8/2004 | Kamoto et al. | |
| 2004/0157612 A1 | 8/2004 | Kim | |
| 2004/0158358 A1* | 8/2004 | Anezaki | G05D 1/0221 700/264 |
| 2004/0162637 A1 | 8/2004 | Wang et al. | |
| 2004/0167666 A1* | 8/2004 | Wang | G06F 19/3418 700/245 |
| 2004/0167668 A1* | 8/2004 | Wang | G06F 19/3418 700/248 |
| 2004/0168148 A1 | 8/2004 | Goncalves et al. | |
| 2004/0170300 A1 | 9/2004 | Jouppi | |
| 2004/0172301 A1 | 9/2004 | Mihai et al. | |
| 2004/0172306 A1 | 9/2004 | Wohl et al. | |
| 2004/0174129 A1 | 9/2004 | Wang et al. | |
| 2004/0175684 A1 | 9/2004 | Kaasa et al. | |
| 2004/0179714 A1 | 9/2004 | Jouppi | |

(56) References Cited

U.S. PATENT DOCUMENTS

| | | |
|---|---|---|
| 2004/0186623 A1 | 9/2004 | Dooley et al. |
| 2004/0189700 A1* | 9/2004 | Mandavilli ......... G06F 3/04845 |
| | | 715/751 |
| 2004/0201602 A1 | 10/2004 | Mody et al. |
| 2004/0205664 A1 | 10/2004 | Prendergast |
| 2004/0215490 A1 | 10/2004 | Duchon et al. |
| 2004/0218099 A1* | 11/2004 | Washington ............ H04N 5/77 |
| | | 348/571 |
| 2004/0222638 A1 | 11/2004 | Bednyak |
| 2004/0224676 A1 | 11/2004 | Iseki |
| 2004/0230340 A1 | 11/2004 | Fukuchi et al. |
| 2004/0240981 A1 | 12/2004 | Dothan et al. |
| 2004/0241981 A1 | 12/2004 | Doris et al. |
| 2004/0260790 A1 | 12/2004 | Balloni et al. |
| 2005/0003330 A1 | 1/2005 | Asgarinejad et al. |
| 2005/0004708 A1 | 1/2005 | Goldenberg et al. |
| 2005/0007445 A1* | 1/2005 | Foote ..................... H04N 7/142 |
| | | 348/14.08 |
| 2005/0013149 A1 | 1/2005 | Trossell |
| 2005/0021182 A1 | 1/2005 | Wang et al. |
| 2005/0021183 A1 | 1/2005 | Wang et al. |
| 2005/0021187 A1 | 1/2005 | Wang et al. |
| 2005/0021309 A1 | 1/2005 | Alexander et al. |
| 2005/0024485 A1 | 2/2005 | Castles et al. |
| 2005/0027567 A1 | 2/2005 | Taha |
| 2005/0027794 A1 | 2/2005 | Decker |
| 2005/0028221 A1* | 2/2005 | Liu ....................... H04N 7/147 |
| | | 725/133 |
| 2005/0035862 A1 | 2/2005 | Wildman et al. |
| 2005/0038416 A1 | 2/2005 | Wang et al. |
| 2005/0038564 A1 | 2/2005 | Burick |
| 2005/0041123 A1 | 2/2005 | Ansari et al. |
| 2005/0049898 A1 | 3/2005 | Hirakawa |
| 2005/0052527 A1 | 3/2005 | Remy et al. |
| 2005/0060211 A1 | 3/2005 | Xiao et al. |
| 2005/0065435 A1 | 3/2005 | Rauch et al. |
| 2005/0065438 A1 | 3/2005 | Miller |
| 2005/0065659 A1 | 3/2005 | Tanaka et al. |
| 2005/0065813 A1 | 3/2005 | Mishelevich et al. |
| 2005/0071046 A1 | 3/2005 | Miyazaki et al. |
| 2005/0073575 A1 | 4/2005 | Thacher et al. |
| 2005/0078816 A1 | 4/2005 | Sekiguchi et al. |
| 2005/0083011 A1 | 4/2005 | Yang et al. |
| 2005/0099493 A1 | 5/2005 | Chew |
| 2005/0104964 A1 | 5/2005 | Bovyrin et al. |
| 2005/0110867 A1 | 5/2005 | Schulz |
| 2005/0122390 A1 | 6/2005 | Wang et al. |
| 2005/0125083 A1 | 6/2005 | Kiko |
| 2005/0125098 A1 | 6/2005 | Wang et al. |
| 2005/0149364 A1 | 7/2005 | Ombrellaro |
| 2005/0152447 A1 | 7/2005 | Jouppi et al. |
| 2005/0152565 A1 | 7/2005 | Jouppi et al. |
| 2005/0154265 A1 | 7/2005 | Miro et al. |
| 2005/0168568 A1 | 8/2005 | Jouppi |
| 2005/0182322 A1 | 8/2005 | Grispo |
| 2005/0192721 A1 | 9/2005 | Jouppi |
| 2005/0204438 A1 | 9/2005 | Wang et al. |
| 2005/0212478 A1 | 9/2005 | Takenaka |
| 2005/0219356 A1* | 10/2005 | Smith .................. A47B 21/0073 |
| | | 348/14.05 |
| 2005/0225634 A1* | 10/2005 | Brunetti ........... G08B 13/19608 |
| | | 348/143 |
| 2005/0231156 A1 | 10/2005 | Yan |
| 2005/0231586 A1 | 10/2005 | Rodman et al. |
| 2005/0232647 A1 | 10/2005 | Takenaka |
| 2005/0234592 A1 | 10/2005 | Mcgee et al. |
| 2005/0237385 A1* | 10/2005 | Kosaka .................. G01B 11/00 |
| | | 348/42 |
| 2005/0264649 A1 | 12/2005 | Chang et al. |
| 2005/0267826 A1 | 12/2005 | Levy et al. |
| 2005/0283414 A1 | 12/2005 | Fernandes et al. |
| 2005/0286759 A1 | 12/2005 | Zitnick et al. |
| 2006/0007943 A1 | 1/2006 | Fellman |
| 2006/0010028 A1 | 1/2006 | Sorensen |
| 2006/0013263 A1 | 1/2006 | Fellman |
| 2006/0013469 A1 | 1/2006 | Wang et al. |
| 2006/0013488 A1 | 1/2006 | Inoue |
| 2006/0014388 A1 | 1/2006 | Lur et al. |
| 2006/0020694 A1 | 1/2006 | Nag et al. |
| 2006/0029065 A1 | 2/2006 | Fellman |
| 2006/0047361 A1* | 3/2006 | Sato ........................ B25J 5/007 |
| | | 700/245 |
| 2006/0047365 A1 | 3/2006 | Ghodoussi et al. |
| 2006/0048286 A1* | 3/2006 | Donato .................. A42B 3/042 |
| | | 2/422 |
| 2006/0052676 A1 | 3/2006 | Wang et al. |
| 2006/0052684 A1 | 3/2006 | Takahashi et al. |
| 2006/0056655 A1 | 3/2006 | Wen et al. |
| 2006/0056837 A1 | 3/2006 | Vapaakoski |
| 2006/0064212 A1 | 3/2006 | Thorne |
| 2006/0066609 A1 | 3/2006 | Iodice et al. |
| 2006/0071797 A1 | 4/2006 | Rosenfeld et al. |
| 2006/0074525 A1 | 4/2006 | Close et al. |
| 2006/0074719 A1 | 4/2006 | Horner |
| 2006/0082642 A1* | 4/2006 | Wang ..................... H04N 7/142 |
| | | 348/14.05 |
| 2006/0087746 A1 | 4/2006 | Lipow |
| 2006/0095158 A1 | 5/2006 | Lee et al. |
| 2006/0095170 A1 | 5/2006 | Yang et al. |
| 2006/0098573 A1 | 5/2006 | Beer et al. |
| 2006/0103659 A1 | 5/2006 | Karandikar et al. |
| 2006/0104279 A1 | 5/2006 | Fellman et al. |
| 2006/0106493 A1 | 5/2006 | Niemeyer et al. |
| 2006/0107223 A1* | 5/2006 | Mirtich .................. G06F 9/451 |
| | | 715/764 |
| 2006/0122482 A1 | 6/2006 | Mariotti et al. |
| 2006/0125356 A1 | 6/2006 | Meek et al. |
| 2006/0142983 A1 | 6/2006 | Sorensen et al. |
| 2006/0149418 A1 | 7/2006 | Anvari |
| 2006/0161136 A1 | 7/2006 | Anderson |
| 2006/0161303 A1 | 7/2006 | Wang et al. |
| 2006/0164546 A1 | 7/2006 | Adachi |
| 2006/0171515 A1 | 8/2006 | Hintermeister et al. |
| 2006/0173708 A1 | 8/2006 | Vining et al. |
| 2006/0173712 A1 | 8/2006 | Joubert |
| 2006/0178559 A1 | 8/2006 | Kumar et al. |
| 2006/0178776 A1 | 8/2006 | Feingold et al. |
| 2006/0178777 A1 | 8/2006 | Park et al. |
| 2006/0189393 A1 | 8/2006 | Edery |
| 2006/0195569 A1 | 8/2006 | Barker |
| 2006/0224781 A1 | 10/2006 | Tsao et al. |
| 2006/0247045 A1 | 11/2006 | Jeong et al. |
| 2006/0259193 A1 | 11/2006 | Wang et al. |
| 2006/0268704 A1 | 11/2006 | Ansari et al. |
| 2006/0271238 A1 | 11/2006 | Choi et al. |
| 2006/0271400 A1 | 11/2006 | Clements et al. |
| 2006/0293788 A1 | 12/2006 | Pogodin |
| 2007/0021871 A1 | 1/2007 | Wang et al. |
| 2007/0025711 A1 | 2/2007 | Marcus |
| 2007/0046237 A1 | 3/2007 | Lakshmanan et al. |
| 2007/0050937 A1 | 3/2007 | Song et al. |
| 2007/0064092 A1 | 3/2007 | Sandberg et al. |
| 2007/0078566 A1 | 4/2007 | Wang et al. |
| 2007/0093279 A1 | 4/2007 | Janik |
| 2007/0112700 A1 | 5/2007 | Den et al. |
| 2007/0116152 A1 | 5/2007 | Thesling |
| 2007/0117516 A1 | 5/2007 | Saidi et al. |
| 2007/0120965 A1 | 5/2007 | Sandberg et al. |
| 2007/0122783 A1 | 5/2007 | Habashi |
| 2007/0133407 A1 | 6/2007 | Choi et al. |
| 2007/0135967 A1 | 6/2007 | Jung et al. |
| 2007/0142964 A1 | 6/2007 | Abramson |
| 2007/0170886 A1 | 7/2007 | Plishner |
| 2007/0176060 A1 | 8/2007 | White et al. |
| 2007/0192910 A1 | 8/2007 | Vu et al. |
| 2007/0197896 A1 | 8/2007 | Moll et al. |
| 2007/0198128 A1 | 8/2007 | Ziegler et al. |
| 2007/0198130 A1 | 8/2007 | Wang et al. |
| 2007/0199108 A1 | 8/2007 | Angle et al. |
| 2007/0216347 A1 | 9/2007 | Kaneko et al. |
| 2007/0226949 A1 | 10/2007 | Hahm et al. |
| 2007/0250212 A1 | 10/2007 | Halloran et al. |
| 2007/0255706 A1 | 11/2007 | Iketani et al. |

(56) References Cited

U.S. PATENT DOCUMENTS

| | | |
|---|---|---|
| 2007/0262884 A1 | 11/2007 | Goncalves et al. |
| 2007/0273751 A1 | 11/2007 | Sachau |
| 2007/0290040 A1 | 12/2007 | Wurman et al. |
| 2007/0291109 A1 | 12/2007 | Wang et al. |
| 2007/0291128 A1 | 12/2007 | Wang et al. |
| 2008/0009969 A1 | 1/2008 | Bruemmer et al. |
| 2008/0011904 A1 | 1/2008 | Cepollina et al. |
| 2008/0027591 A1 | 1/2008 | Lenser et al. |
| 2008/0033641 A1 | 2/2008 | Medalia |
| 2008/0045804 A1 | 2/2008 | Williams |
| 2008/0051985 A1 | 2/2008 | D Andrea et al. |
| 2008/0065268 A1 | 3/2008 | Wang et al. |
| 2008/0082211 A1 | 4/2008 | Wang et al. |
| 2008/0086241 A1 | 4/2008 | Phillips et al. |
| 2008/0091340 A1 | 4/2008 | Milstein et al. |
| 2008/0126132 A1 | 5/2008 | Warner et al. |
| 2008/0133052 A1 | 6/2008 | Jones et al. |
| 2008/0161969 A1 | 7/2008 | Lee et al. |
| 2008/0174570 A1 | 7/2008 | Jobs et al. |
| 2008/0201016 A1 | 8/2008 | Finlay |
| 2008/0201017 A1 | 8/2008 | Wang et al. |
| 2008/0215987 A1 | 9/2008 | Alexander et al. |
| 2008/0229531 A1 | 9/2008 | Takida |
| 2008/0232763 A1 | 9/2008 | Brady |
| 2008/0255703 A1 | 10/2008 | Wang et al. |
| 2008/0263451 A1 | 10/2008 | Portele et al. |
| 2008/0263628 A1 | 10/2008 | Norman et al. |
| 2008/0267069 A1 | 10/2008 | Thielman et al. |
| 2008/0269949 A1 | 10/2008 | Norman et al. |
| 2008/0281467 A1 | 11/2008 | Pinter |
| 2008/0306375 A1 | 12/2008 | Sayler et al. |
| 2009/0030552 A1 | 1/2009 | Nakadai et al. |
| 2009/0044334 A1 | 2/2009 | Parsell et al. |
| 2009/0049640 A1 | 2/2009 | Lee et al. |
| 2009/0055023 A1 | 2/2009 | Walters et al. |
| 2009/0070135 A1 | 3/2009 | Parida et al. |
| 2009/0086013 A1 | 4/2009 | Thapa |
| 2009/0102919 A1 | 4/2009 | Zamierowski et al. |
| 2009/0105882 A1 | 4/2009 | Wang et al. |
| 2009/0106679 A1 | 4/2009 | Anzures et al. |
| 2009/0122699 A1 | 5/2009 | Alperovitch et al. |
| 2009/0125147 A1 | 5/2009 | Wang et al. |
| 2009/0144425 A1 | 6/2009 | Marr et al. |
| 2009/0164255 A1 | 6/2009 | Menschik et al. |
| 2009/0164657 A1 | 6/2009 | Li et al. |
| 2009/0171170 A1 | 7/2009 | Li et al. |
| 2009/0177323 A1 | 7/2009 | Ziegler et al. |
| 2009/0177641 A1 | 7/2009 | Raghavan |
| 2009/0237317 A1 | 9/2009 | Rofougaran |
| 2009/0240371 A1 | 9/2009 | Wang et al. |
| 2009/0248200 A1 | 10/2009 | Root |
| 2009/0259339 A1 | 10/2009 | Wright et al. |
| 2010/0010672 A1 | 1/2010 | Wang et al. |
| 2010/0010673 A1 | 1/2010 | Wang et al. |
| 2010/0017046 A1 | 1/2010 | Cheung et al. |
| 2010/0019715 A1 | 1/2010 | Roe et al. |
| 2010/0026239 A1 | 2/2010 | Li et al. |
| 2010/0030578 A1 | 2/2010 | Siddique et al. |
| 2010/0051596 A1 | 3/2010 | Diedrick et al. |
| 2010/0063848 A1 | 3/2010 | Kremer et al. |
| 2010/0066804 A1 | 3/2010 | Shoemake et al. |
| 2010/0070079 A1 | 3/2010 | Mangaser et al. |
| 2010/0073490 A1 | 3/2010 | Wang et al. |
| 2010/0076600 A1 | 3/2010 | Cross et al. |
| 2010/0085874 A1 | 4/2010 | Noy et al. |
| 2010/0088232 A1 | 4/2010 | Gale |
| 2010/0115418 A1 | 5/2010 | Wang et al. |
| 2010/0116566 A1 | 5/2010 | Ohm et al. |
| 2010/0131103 A1 | 5/2010 | Herzog et al. |
| 2010/0145479 A1 | 6/2010 | Griffiths |
| 2010/0157825 A1 | 6/2010 | Anderlind et al. |
| 2010/0171826 A1 | 7/2010 | Hamilton et al. |
| 2010/0191375 A1 | 7/2010 | Wright et al. |
| 2010/0228249 A1 | 9/2010 | Mohr et al. |
| 2010/0268383 A1 | 10/2010 | Wang et al. |
| 2010/0278086 A1 | 11/2010 | Pochiraju et al. |
| 2010/0286905 A1 | 11/2010 | Goncalves et al. |
| 2010/0301679 A1 | 12/2010 | Murray et al. |
| 2010/0323783 A1 | 12/2010 | Nonaka et al. |
| 2011/0022705 A1 | 1/2011 | Yellamraju et al. |
| 2011/0050841 A1 | 3/2011 | Wang et al. |
| 2011/0071675 A1 | 3/2011 | Wells et al. |
| 2011/0071702 A1 | 3/2011 | Wang et al. |
| 2011/0072114 A1 | 3/2011 | Hoffert et al. |
| 2011/0153198 A1 | 6/2011 | Kokkas et al. |
| 2011/0172822 A1 | 7/2011 | Ziegler et al. |
| 2011/0187875 A1 | 8/2011 | Sanchez et al. |
| 2011/0190930 A1 | 8/2011 | Hanrahan et al. |
| 2011/0193949 A1 | 8/2011 | Nambakam et al. |
| 2011/0195701 A1 | 8/2011 | Cook et al. |
| 2011/0213210 A1 | 9/2011 | Temby et al. |
| 2011/0218674 A1 | 9/2011 | Stuart et al. |
| 2011/0245973 A1 | 10/2011 | Wang et al. |
| 2011/0280551 A1 | 11/2011 | Sammon |
| 2011/0292193 A1 | 12/2011 | Wang et al. |
| 2011/0301759 A1 | 12/2011 | Wang et al. |
| 2011/0306400 A1 | 12/2011 | Nguyen |
| 2012/0023506 A1 | 1/2012 | Maeckel et al. |
| 2012/0036484 A1 | 2/2012 | Zhang et al. |
| 2012/0059946 A1 | 3/2012 | Wang |
| 2012/0072023 A1 | 3/2012 | Ota |
| 2012/0072024 A1 | 3/2012 | Wang et al. |
| 2012/0092157 A1 | 4/2012 | Tran |
| 2012/0095352 A1 | 4/2012 | Tran |
| 2012/0113856 A1 | 5/2012 | Krishnaswamy |
| 2012/0191246 A1 | 7/2012 | Roe et al. |
| 2012/0191464 A1 | 7/2012 | Stuart et al. |
| 2012/0203731 A1 | 8/2012 | Nelson et al. |
| 2012/0291809 A1 | 11/2012 | Kuhe et al. |
| 2013/0250938 A1 | 9/2013 | Anandakumar et al. |
| 2014/0047022 A1 | 2/2014 | Chan et al. |
| 2014/0085543 A1 | 3/2014 | Hartley et al. |
| 2014/0135990 A1 | 5/2014 | Stuart et al. |
| 2014/0139616 A1 | 5/2014 | Pinter et al. |
| 2014/0155755 A1 | 6/2014 | Pinter et al. |

FOREIGN PATENT DOCUMENTS

| | | |
|---|---|---|
| CN | 1404695 A | 3/2003 |
| CN | 1554193 A | 12/2004 |
| CN | 1554985 A | 12/2004 |
| CN | 1561923 A | 1/2005 |
| CN | 1743144 A | 3/2006 |
| CN | 101049017 A | 10/2007 |
| CN | 101106939 A | 1/2008 |
| CN | 101151614 A | 3/2008 |
| CN | 100407729 C | 7/2008 |
| CN | 101390098 A | 3/2009 |
| CN | 101507260 A | 8/2009 |
| CN | 101730894 A | 6/2010 |
| CN | 101866396 A | 10/2010 |
| CN | 101978365 A | 2/2011 |
| CN | 102203759 A | 9/2011 |
| CN | 101106939 B | 11/2011 |
| EP | 466492 A2 | 1/1992 |
| EP | 488673 A2 | 6/1992 |
| EP | 0981905 B1 | 1/2002 |
| EP | 1262142 A2 | 12/2002 |
| EP | 1304872 A1 | 4/2003 |
| EP | 1536660 A2 | 6/2005 |
| EP | 1573406 A2 | 9/2005 |
| EP | 1594660 A2 | 11/2005 |
| EP | 1763243 A2 | 3/2007 |
| EP | 1791464 A2 | 6/2007 |
| EP | 1800476 A2 | 6/2007 |
| EP | 1819108 A2 | 8/2007 |
| EP | 1856644 A2 | 11/2007 |
| EP | 1536660 A3 | 4/2008 |
| EP | 1928310 A2 | 6/2008 |
| EP | 1232610 B1 | 1/2009 |
| EP | 2027716 A2 | 2/2009 |
| EP | 2145274 A1 | 1/2010 |
| EP | 2214111 A2 | 8/2010 |
| EP | 2263158 A2 | 12/2010 |

(56) References Cited

FOREIGN PATENT DOCUMENTS

| | | |
|---|---|---|
| EP | 2300930 A1 | 3/2011 |
| EP | 2342651 A1 | 7/2011 |
| GB | 2285361 A | 7/1995 |
| GB | 2431261 A | 4/2007 |
| JP | 7194609 A | 8/1995 |
| JP | 7213753 A | 8/1995 |
| JP | 7248823 A | 9/1995 |
| JP | 7257422 A | 10/1995 |
| JP | 884328 A | 3/1996 |
| JP | 8320727 A | 12/1996 |
| JP | 9267276 A | 10/1997 |
| JP | 1079097 A | 3/1998 |
| JP | 10288689 A | 10/1998 |
| JP | 11220706 A | 8/1999 |
| JP | 2000-032319 A | 1/2000 |
| JP | 2000-049800 A | 2/2000 |
| JP | 2000-079587 A | 3/2000 |
| JP | 2000-196876 A | 7/2000 |
| JP | 2001-125641 A | 5/2001 |
| JP | 2001-147718 A | 5/2001 |
| JP | 2001-179663 A | 7/2001 |
| JP | 2001-188124 A | 7/2001 |
| JP | 2001-198865 A | 7/2001 |
| JP | 2001-198868 A | 7/2001 |
| JP | 2001-199356 A | 7/2001 |
| JP | 2002-000574 A | 1/2002 |
| JP | 2002-046088 A | 2/2002 |
| JP | 2002-101333 A | 4/2002 |
| JP | 2002-112970 A | 4/2002 |
| JP | 2002-235423 A | 8/2002 |
| JP | 2002-305743 A | 10/2002 |
| JP | 2002-321180 A | 11/2002 |
| JP | 2002-355779 A | 12/2002 |
| JP | 2004-181229 A | 7/2004 |
| JP | 2004-524824 A | 8/2004 |
| JP | 2004-261941 A | 9/2004 |
| JP | 2004-289379 A | 10/2004 |
| JP | 2005-028066 A | 2/2005 |
| JP | 2005-059170 A | 3/2005 |
| JP | 2005-111083 A | 4/2005 |
| JP | 2006-508806 A | 3/2006 |
| JP | 2006-109094 A | 4/2006 |
| JP | 2006-224294 A | 8/2006 |
| JP | 2006-246438 A | 9/2006 |
| JP | 2007-007040 A | 1/2007 |
| JP | 2007-081646 A | 3/2007 |
| JP | 2007-232208 A | 9/2007 |
| JP | 2007-316966 A | 12/2007 |
| JP | 2009-125133 A | 6/2009 |
| JP | 2010-064154 A | 3/2010 |
| JP | 2010-532109 A | 9/2010 |
| JP | 2010-246954 A | 11/2010 |
| KR | 20060037979 A | 5/2006 |
| KR | 20090012542 A | 2/2009 |
| KR | 20100019479 A | 2/2010 |
| KR | 20100139037 A | 12/2010 |
| WO | 93/06690 A1 | 4/1993 |
| WO | 97/042761 A1 | 11/1997 |
| WO | 98/43424 A1 | 10/1998 |
| WO | 1998/051078 A1 | 11/1998 |
| WO | 99/067067 A1 | 12/1999 |
| WO | 2000/025516 A1 | 5/2000 |
| WO | 2000/033726 A1 | 6/2000 |
| WO | 0131861 A1 | 5/2001 |
| WO | 2003/077745 A1 | 9/2003 |
| WO | 2004/008738 A1 | 1/2004 |
| WO | 2004/012018 A2 | 2/2004 |
| WO | 2004/075456 A2 | 9/2004 |
| WO | 2006/012797 A1 | 2/2006 |
| WO | 2006/044847 A2 | 4/2006 |
| WO | 2006/078611 A2 | 7/2006 |
| WO | 2007/041295 A2 | 4/2007 |
| WO | 2007/041038 A3 | 6/2007 |
| WO | 2008/100272 A2 | 8/2008 |
| WO | 2008/100272 A3 | 10/2008 |
| WO | 2009/117274 A2 | 9/2009 |
| WO | 2009/128997 A1 | 10/2009 |
| WO | 2009/145958 A2 | 12/2009 |
| WO | 2010/006205 A1 | 1/2010 |
| WO | 2010/006211 A1 | 1/2010 |
| WO | 2010/033666 A1 | 3/2010 |
| WO | 2010/047881 A1 | 4/2010 |
| WO | 2010/062798 A1 | 6/2010 |
| WO | 2010/065257 A1 | 6/2010 |
| WO | 2010/120407 A1 | 10/2010 |
| WO | 2011/028589 A2 | 3/2011 |
| WO | 2011/028589 A3 | 4/2011 |
| WO | 2011/097130 A2 | 8/2011 |
| WO | 2011/097132 A2 | 8/2011 |
| WO | 2011/109336 A2 | 9/2011 |
| WO | 2011/097132 A3 | 12/2011 |
| WO | 2011/149902 A2 | 12/2011 |

OTHER PUBLICATIONS

Paulos et al., "Ubiquitous Tele-Embodiment: Applications and Implications", International Journal of Human Computer Studies, vol. 46, No. 6, Jun. 1997, pp. 861-877.

Paulos, "Video of PRoP 2 at Richmond Field Station", www.prop.org Printout of Home Page of Website and two-page Transcript of the audio portion of said PRoP Video, May 2001.

International Preliminary Report on Patentability and Written Opinion received for PCT Patent Application No. PCT/US2005/037347, dated Apr. 17, 2006, 7 pages.

International Preliminary Report on Patentability and Written Opinion received for PCT Patent Application No. PCT/US2006/037076, dated Apr. 1, 2008, 6 pages.

International Search Report and Written Opinion received for PCT Application No. PCT/US2006/037076, dated May 11, 2007, 6 pages.

International Preliminary Report on Patentability received for PCT Patent Application No. PCT/US/2007/014099, dated Dec. 16, 2008, 5 pages.

International Search Report received for PCT Patent Application No. PCT/US2007/014099, dated Jul. 30, 2008, 1 page.

PictureTel Corporation, "PictureTel Live200 for Windows NT Product Guide", 1997, 63 pages.

Pin et al., "A New Family of Omnidirectional and Holonomic Wheeled Platforms for Mobile Robots", IEEE Transactions on Robotics and Automation, vol. 10, No. 4, Aug. 1994, pp. 480-489.

Piquepaille, Roland, "This Blog and its RSS Feed Are Moving", Roland Piquepaille's Technology Trends, How new technologies are modifying our way of life, Oct. 31, 2004, 2 pages.

Radvision, "Making Sense of Bandwidth the NetsenseWay", Network Congestion in Unmanaged Networks Bandwidth Estimation and Adaptation Techniques,White Paper, Radvision's Netsense Technology, 2010, 7 pages.

Reynolds et al., "Review of Robotic Telemedicine Utilization in Intensive Care Units (ICUs)", 11th Annual ATA Symposium, Tampa, Florida, 2011, 1 page.

Roach, Adam, "Automatic Call Back Service in SIP", Internet Engineering Task Force, Internet Draft, Category: Informational, Mar. 2000, 8 pages.

Rovetta et al., "A New Telerobotic Application: Remote Laparoscopic Surgery Using Satellites and optical fiber Networks for Data Exchange", International Journal of Robotics Research, vol. 15, No. 3, Jun. 1, 1996, pp. 267-279.

Roy et al., "Towards Personal Service Robots for the Elderly", Workshop on Interactive Robots and Entertainment (WIRE 2000), Online available at <http://www.ri.cmu.edu/pb-files/pub2/roy-nicholas-2000-1/roy-nicholas-2000-1.pdf>, vol. 25, Apr. 30-May 1, 2000, 7 pages.

Sachs et al., "Virtual Visit: Improving Communication for Those Who Need it Most", Studies in Health Technology and Informatics, vol. 94, Medicine Meets Virtual Reality 11, 2003, pp. 302-308.

Salemi et al., "MILO: Personal Robot Platform", IEEE/RSJ International Conference on Intelligent Robots and Systems, Aug. 2005, pp. 4089-4094.

(56) References Cited

OTHER PUBLICATIONS

Sandt et al., "Perceptions for a Transport Robot in Public Environments", Proceedings of the 1997 IEEE/RSJ International Conference on Intelligent Robots and Systems, vol. 1, Sep. 7-11, 1997, pp. 360-365.
Sawyer, Robert J., "Inventing the Future: 2000 Years of Discovery", Available online at <http://www.sfwriter.com/pritf.htm>, Retrieved on May 25, 2008, Jan. 2, 2000, 2 pages.
Schaeffer et al., "Care-O-BotTM: The Concept of a System for Assisting Elderly or Disabled Persons in Home Environments", Proceedings of the 24th Annual Conference of the IEEE Industrial Electronics Society, vol. 4, 1998, pp. 2476-2481.
Schraft et al., "Care-O-bot: the Concept of a System for Assisting Elderly or Disabled Persons in Home Enviornments", IEEE Proceedings of the 24th Annual Conference of the Industrial Electronics Society, IECON '98, Aug. 31-Sep. 4, 1998, pp. 2476-2481.
Schultz et al., "Web Interfaces for Mobile Robots in Public Places", IEEE Robotics and Automation Magazine, vol. 7 , No. 1, Mar. 2000, pp. 48-56.
Shimoga et al., "Touch and Force Reflection for Telepresence Surgery", Proceedings of the 16th Annual International Conference of the IEEE Engineering in Medicine and Biology Society, Nov. 1994, pp. 1049-1050.
Siegwart et al., "Interacting Mobile Robots on the Web", Proceedings of the 1999 IEEE International Conference on Robotics and Automation, May 1999, pp. 1-7.
Simmons et al., "Xavier: An Autonomous Mobile Robot on the Web", IEEE Robotics and Automation Magazine, 1999, pp. 43-48.
Stephenson, Gary, "Dr. Robot Tested at Hopkins", Available at <http://www.hopkinsmedicine.org/press/2003/august/030805.htm>, Aug. 5, 2003, 2 pages.
Stoianovici et al., "Robotic Tools for Minimally Invasive Urologic Surgery", Complications of Urologic Laparoscopic Surgery: Recognition, Management and Prevention, Dec. 2002, 17 pages.
Suplee, Curt, "Mastering the Robot", The Washington Post, Washington Post Staff Writer, Sep. 17, 2000, 5 pages.
Tahboub et al., "Dynamics Analysis and Control of a Holonomic Vehicle With Continuously Variable Transmission", Transactions of the ASME , Journal of Dynamic Systems, Measurement and Control, vol. 124, Mar. 2002, pp. 118-126.
Telepresence Research, Inc., "The Telepresence Mobile Robot System", Available at <http://www.telepresence.com/telepresence-research/TELEROBOT/>, Retrieved on Nov. 23, 2010, Feb. 20, 1995, 3 pages.
Tendick et al., "Human-Machine Interfaces for Minimally Invasive Surgery", vol. 6, Proceedings of the 19th Annual International Conference of the IEEE Engineering in Medicine and Biology Society, Oct. 30-Nov. 2, 1997, pp. 2771-2776.
Theodosiou et al., "MuLVAT: A Video Annotation Tool Based on XML-Dictionaries and Shot Clustering", Part II, 19th International Conference, Artificial Neural Networks—ICANN 2009, Sep. 14-17, 2009, pp. 913-922.
Thrun et al., "Probabilistic Algorithms and the Interactive Museum Tour-Guide Robot Minerva", vol. 19, International Journal of Robotics Research, 2000, pp. 1-35.
Time, Lists, "Office Coworker Robot", Best Inventions of 2001, Available at <http://content.time.com/time/specials/packages/article/0,28804,1936165_1936255_1936640,00.html>, Nov. 19, 2001, 2 pages.
Tipsuwan et al., "Gain Adaptation of Networked Mobile Robot to Compensate QoS Deterioration", 28th Annual Conference of the Industrial Electronics Society, vol. 4, Nov. 5-8, 2002, pp. 3146-3151.
Tsui et al., "Exploring Use Cases for Telepresence Robots", 6th ACM/IEEE International Conference on Human-Robot Interaction (HRI), Mar. 2011, pp. 11-18.
Tyrrell et al., "Teleconsultation in Psychology: The Use of Videolinks for Interviewing and Assessing Elderly Patients", Age and Ageing, vol. 30, No. 3, May 2001, pp. 191-195.
Tzafestas et al., "VR-Based Teleoperation of a Mobile Robotic Assistant: Progress Report", Technical Report DEMO 2000/13, Institute of Informatics and Telecommunications, National Center for Scientific Research "Demokritos", Nov. 2000, pp. 1-23.
UMASS Lowell Robotics Lab, "Robotics Lab at UMASS Lowell", Brochure, 2011, 2 pages.
Urquhart, Kim, "InTouch's Robotic Companion 'Beams Up' Healthcare Experts", Medical Device Daily, vol. 7, No. 39, Feb. 27, 2003, pp. 1, 4.
Video Middleware Cookbook, "H.350 Directory Services for Multimedia", 2 pages.
Weaver et al., "Monitoring and Controlling Using the Internet and Java", Proceedings of the 25th Annual Conference of the IEEE Industrial Electronics Society, vol. 3, 1999, pp. 1152-1158.
Weiss et al., "PEBBLES: A Personal Technology for Meeting Education, Social and Emotional Needs of Hospitalised Children", Personal and Ubiquitous Computing, vol. 5, No. 3, Aug. 2001, pp. 157-168.
Weiss et al., "Telework and Video-Mediated Communication: Importance of Real-Time, Interactive Communication for Workers with Disabilities", Available at <http://www.telbotics.com/research-3.htm>, Retrieved on Nov. 23, 2010, 3 pages.
West et al., "Design of Ball Wheel Mechanisms for Omnidirectional Vehicles with Full Mobility and Invariant Kinematics", Journal of Mechanical Design , vol. 119, Jun. 1997, pp. 153-161.
Yamasaki et al., "Applying Personal Robots and Active Interface to Video Conference Systems", 6th International Conference on Human Computer Interaction, vol. 20, Issue B, 1995, pp. 243-248.
Yamauchi, Brian, "PackBot: A Versatile Platform for Military Robotics", Proceedings of SPIE for Military Robotics, 2004, pp. 228-237.
Yong et al., "Robot Task Execution with Telepresence Using Virtual Reality Technology", 1998 International Conference on Mechatronic Technology, Nov. 30-Dec. 2, 1998, pp. 1-8.
Zambroski, James, "CMU, Pitt Developing 'Nursebot'", Available at <http://www.cs.cmu.edu/nursebot/web/press/tribunereview.html>, Retrieved on Jun. 26, 2012, Oct. 27, 2000, 3 pages.
Cleary et al., "State of the Art in Surgical Robotics: Clinical Applications and Technology Challenges", Feb. 24, 2002, pp. 1-26.
CMU Course 16×62, "Robot user's manual", (describing the Nomad Scout), Carnegie Mellon University, Feb. 1, 2001, 11 pages.
CNN, "Floating 'Droids' to Roam Space Corridors of the Future", Available online at <http://edition.cnn.com/2000/TECH/space/01/12/psa/>, Retrieved on Nov. 11, 2010, Jan. 12, 2000, 3 pages.
cnn.com, "Paging Dr.Robot: Machine Helps Doctors with Patients", Sep. 30, 2003, 3 pages.
Crowley, Susan L., "Hello to Our Future", AARP Bulletin, Jan. 2000, 12 pages.
Dalton, Barnaby, "Techniques for Web Telerobotics", PhD Thesis, University of Western Australia, 2001, 243 pages.
Dario et al., "A Robot Workstation for Diagnosis and Physical Therapy", IEEE Catalog No. 88TH0234-5, 1989, pp. 67-72.
Davies, Brian, "Robotics in Minimally Invasive Surgery", Mechatronics in Medicine Lab, Dept Mechanical Engineering, Imperial College, London SW7 2BX, 1995, pp. 1-2.
Davis, Erik, "Telefriend, Meet iRobot, The Smartest Webcam on Wheels", Wired Magazine, Issue 8.09, Available at < http://www.wired.com/wired/archive/8.09/irobot.html?pg=1ANDtopic=ANDtopicset=>, Sep. 2000, 3 pages.
Dean et al., "1992 AAAI Robot Exhibition and Competition", Articles, AI Magazine, vol. 14, No. 1, 1993, 15 pages.
Digiorgio, James, "Is Your Emergency Department of the Leading Edge?", Chicago Hospital News, vol. 2, No. 12, 2005, 3 pages.
Dudenhoeffer et al., "Command and Control Architectures for Autonomous Micro-Robotic Forces", FY00 Project Report, Idaho National Engineering and Environmental Laboratory Human Systems Engineering and Sciences Department, Idaho Falls, Apr. 2001, 43 pages.
Elhajj et al., "Real-Time Haptic Feedback in Internet-Based Telerobotic Operation", IEEE International Conference on Electro/Information Technology, Available online at <http://www.egr.msu.edu/ralab-web/cgi-bin/internet-teleoperation.php>, Jun. 2000, 10 pages.

(56) References Cited

OTHER PUBLICATIONS

Elhajj et al., "Supermedia in Internet-Based Telerobotic Operations", Management of Multimedia on the Internet Lecture Notes in Computer Science, vol. 2216, Springer-Verlag Berlin Heidelberg, Oct. 29-Nov. 1, 2001, pp. 359-372.
Elhajj et al., "Synchronization and Control of Supermedia Transmission Via the Internet", Proceedings of 2001 International Symposium on Intelligent Multimedia Video and Speech Processing, May 2-4, 2001, pp. 320-323.
Ellison et al., "Telerounding and Patient Satisfaction Following Surgery", 2004, pp. 523-530.
Evans et al., "The Trackless Robotic Courier", PYXIS HelpMate, 2007, 3 pages.
Fels et al., "Developing a Video-Mediated Communication System for Hospitalized Children", Telemedicine Journal, vol. 5, No. 2, 1999, 30 pages.
Fetterman et al., "Videoconferencing Over the Internet", 2001, 8 pages.
Fiorini et al., "Health Care Robotics: A Progress Report", IEEE International Conference on Robotics and Automation, Apr. 20-25, 1997, pp. 1271-1276.
Fong, Terrence, "Collaborative Control: A Robot-Centric Model for Vehicle Teleoperation", Doctoral Dissertation, Technical Report CMU-RI-TR-01-34, Robotics Institute, Carnegie Mellon University, Nov. 2001, 197 pages.
Fulbright et al., "SWAMI: An Autonomous Mobile Robot for Inspection of Nuclear Waste of Storage Facilities", Autonomous Robots, vol. 2, 1995, pp. 225-235.
Gaidioz et al., "Synchronizing Network Probes to Avoid Measurement Intrusiveness with the Network Weather Service", Proceedings of the Ninth International Symposium on High-Performance Distributed Computing, 2000, pp. 147-154.
Garner et al., "The Application of Telepresence in Medicine", BT Technology Journal, vol. 15, No. 4, Oct. 1, 1997, pp. 181-187.
Ghiasi et al., "A Generic Web-based Teleoperations Architecture: Details and Experience", Proceedings of SPIE, Telemanipulator and Telepresence Technologies VI, vol. 3840, No. 234, Sep. 19, 1999, 14 pages.
Goldberg et al., "Collaborative Teleoperation via the Internet", IEEE International Conference on Robotics and Automation (ICRA), vol. 2, 2000, pp. 2019-2024.
Goldberg et al., "Desktop Teleoperation via the World Wide Web", Robotics and Automation, Proceedings of the 1995 IEEE International Conference, vol. 1, May 21-27, 1995, pp. 654-659.
Goldenberg et al., "Telemedicine in Otolaryngology", American Journal of Otolaryngology, vol. 23, No. 1, 2002, pp. 35-43.
Goldman, Lea, "Machine Dreams", Available Online at <http://www.forbes.com/global/2002/0527/043.html>, retrieved on Nov. 23, 2010, May 27, 2002, 5 pages.
Gostai, "Gostai Jazz: Robotic Telepresence", Available online at <http://www.robotshop.com/media/files/pdf/gostai-jazz-information-sheet.pdf>, 4 pages.
Gump, Michael D., "Robot Technology Improves VA Pharmacies", U.S. Medicine Informational Central, Jul. 2001, 3 pages.
Hameed et al., "A Review of Telemedicine", Journal of Telemedicine and Telecare, vol. 5, Supplement 1, 1999, pp. 103-106.
Han et al., "Construction of an Omnidirectional Mobile Robot Platform Based on Active Dual-Wheel Caster Mechanisms and Development of a Control Simulator", Kluwer Acedemic Publishers, vol. 29, Nov. 2000, pp. 257-275.
Handley et al., "RFC 2327—SDP: Session Description Protocol", Available Online at <http://www.faqs.org/rfcs/rfc2327.html>, Retrieved on Nov. 23, 2010, Apr. 1998, 22 pages.
Hanebeck et al., "ROMAN: A Mobile Robotic Assistant for Indoor Service Applications", Intelligent Robots and Systems, IROS '97, International Conference on Proceedings of the 1997 IEEE/RSJ, vol. 2, Sep. 7-11, 1997, pp. 518-525.
Harmo et al., "Moving Eye—Interactive Telepresence Over Internet With a Ball Shaped Mobile Robot", Available Online at <http://automation.tkk.fi/files/tervetaas/MovingEye4.pdf>, 2000, 6 pages.
Haule et al., "Control Scheme for Delayed Teleoperation Tasks", Communications, Computers, and Signal Processing, Proceedings of IEEE Pacific Rim Conference, May 17-19, 1995, pp. 157-160.
Hees, William P., "Communications Design for a Remote Presence Robot", CSCI E-131b, Final Project, Jan. 14, 2002, 12 pages.
Herias et al., "Flexible Virtual and Remote Laboratory for Teaching Robotics", FORMATEX 2006, Proc. Advance in Control Education Madrid, Spain, Jun. 2006, pp. 1959-1963.
Holmberg, "Development of a Holonomic Mobile Robot for Mobile Manipulation Tasks", The Robotics Laboratory, Computer Science Department, Stanford University, Stanford, California, USA, vol. 19, No. 11, Nov. 2000, pp. 1066-1074.
Ishiguro et al., "Integrating a Perceptual Information Infrastructure with Robotic Avatars: A Framework for Tele-Existence", Intelligent Robots and Systems, IROS '99, Proceedings of 1999 IEEE/RSJ International Conference, vol. 2, 1999, pp. 1032-1038.
Ishihara et al., "Intelligent Microrobot DDS (Drug Delivery System) Measured and Controlled by Ultrasonics", Intelligent Robots and Systems '91, Intelligence for Mechanical Systems, International Workshop on Proceedings of IROS '91 IEEE/RSJ, vol. 2, Nov. 3-5, 1991, pp. 1145-1150.
ITU, "Call Completion Supplementary Services for H.323", ITU-T, Telecommunication Standardization Sector of ITU, H.450.9, Series H: Audiovisual and Multimedia Systems, Nov. 2000, 63 pages.
ITU, "Call Intrusion Supplementary Service for H.323", ITU-T, Telecommunication Standardization Sector of ITU, H.450.11, Series H: Audiovisual and Multimedia Systems, Mar. 2001, 59 pages.
ITU, "Packet-Based Multimedia Communications Systems", ITU-T, Telecommunication Standardization Sector of ITU, H.323, Series H: Audiovisual and Multimedia Systems, Feb. 1998, 128 pages.
ITU, "Transmission of Non-Telephone Signals: A Far End Camera Control Protocol for VideoConferences Using H.224", ITU-T, Telecommunication Standardization Sector of ITU, H.281, Nov. 1994, 12 pages.
Ivanova, Natali, "Master's thesis: Internet Based Interface for Control of a Mobile Robot", Department of Numerical Analysis and Computer Science, 2003, 59 pages.
Jacobs et al., "Applying Telemedicine to Outpatient Physical Therapy", AMIA, Annual Symposium Proceedings, 2002, 1 page.
Jenkins et al., "Telehealth Advancing Nursing Practice", Nursing Outlook, vol. 49, No. 2, Mar. 2001, pp. 100-105.
Johanson, Mathias, "Supporting Video-Mediated Communication Over the Internet", Department of Computer Engineering, Chalmers University of Technology, Gothenburg, Sweden, 2003, 222 pages.
Zamrazil, Kristie, "Telemedicine in Texas: Public Policy Concerns", Focus Report, House Research Organization, Texas House of Representatives, No. 76-22, May 5, 2000, pp. 1-16.
Zipperer, Lorri, "Robotic Dispensing System", ISMP Medication Safety Alert., vol. 4, No. 17, Aug. 25, 1999, 2 pages.
Screenshot Showing Google Date for Lemaire Telehealth Manual, screenshot retrieved on Dec. 18, 2014, 1 page.
Appeal from the U.S. District Court for the Central District of California in case No. 11-cv-9185, Judge Percy Anderson, Joint Appendix, vol. I of IV, Jun. 24, 2013, pp. A1-A6357.
Appeal from the U.S. District Court for the Central District of California in case No. 11-cv-9185, Judge Percy Anderson, Joint Appendix, vol. II of IV, Jun. 24, 2013, pp. A6849-A10634.
Appeal from the U.S. District Court for the Central District of California in case No. 11-cv-9185, Judge Percy Anderson, Joint Appendix, vol. III of IV, Jun. 24, 2013, pp. A10654-A15517.
Appeal from the U.S. District Court for the Central District of California in case No. 11-cv-9185, Judge Percy Anderson, Joint Appendix, vol. IV of IV, Jun. 24, 2013, pp. A15677-A18127.
Appeal from the U.S. District Court for the Central District of California in No. 11-CV-9185, Judge Percy Anderson, May 9, 2014, pp. 1-48.
Civil Minutes-General: Case No. CV 11-9185PA (AJWx), *InTouch Tech., Inc.* v. *VGO Commons, Inc.*, Sep. 10, 2012, 7 pages.
Defendant VGO Communications, Inc.'s Invalidity Contentions Pursuant to the Feb. 27, 2012 Civil Minute Order, May 2, 2012, 143 pages.

(56) References Cited

OTHER PUBLICATIONS

Defendant-Counterclaimant VGO Communications, Inc.'s Supplemental Invalidity Contentions Pursuant to the Feb. 27, 2012 Civil Minute Order, May 14, 2012, 228 pages.
Google translation of: Innovations Report, From research project to television star: Care-O-bot in ZDF series, Online available at <http://www.innovations-report.de/specials/printa.php?id=5157>, Sep. 28, 2001, 2 pages.
Magne Charge, Smart Power for Electric Vehicles, Aug. 26, 1997, 2 pages.
More Online Robots: Robots that Manipulate, available online at <http://ford.ieor.berkeley.edu/ir/robots-a2.html>, Retrieved on Nov. 23, 2010, Aug. 2001, 2 pages.
MPEG File Format Summary, Downloaded from: <http://www.fileformat.info/format/mpeg/egff.htm>, Feb. 1, 2001, 8 pages.
Nomad Scout Language Reference Manual, Nomadic Technologies, Software Version 2.7, Part No. DOC00002, Jul. 12, 1999, 47 pages.
Nomad Scout User's Manual, Nomadic Technologies, Software Version 2. 7, Part No. DOC00004, Jul. 12, 1999, pp. 1-59.
Zorn, Benjamin G., "Ubiquitous Telepresence", Department of Computer Science, University of Colorado, 1996, 13 pages.
Opening Brief for Plaintiff-Appellant InTouch Technologies, Inc., Appeal from the U.S. District Court for the Central District of California in Case No. 11-cv-9185, Judge Percy Anderson, Apr. 12, 2013, 187 pages.
PictureTel Adds New Features and Functionality to Its Award-Winning Live200 Desktop Videoconferencing System, PR Newswire Association, LLC, Gale, Cengage Learning, Jun. 13, 1997, 5 pages.
Reply Brief for Defendant-Appellee VGO Communications, Inc., Appeal from the U.S. District Court for the Central District of California, in Case No. 2:11-cv-9185, Judge Percy Anderson, May 28, 2013, 75 pages.
Reply Brief for Plaintiff-Appellant InTouch Technologies, Inc., Appeal from the U.S. District Court for the Central District of California in Case No. 11-cv-9185, Judge Percy Anderson, Jun. 14, 2013, 39 pages.
Robart I, II, III, Spawar, Systems Center Pacific, 1998, 8 pages.
Using your Infrared Cell Phone Camera, Online available at <http://www.catsdomain.com/xray/about.htm>, Courtesy of Internet Wayback Machine, Jan. 30, 2010, 4 pages.
U.S. Appl. No. 10/783,760, filed Feb. 20, 2004, 48 pages.
Office Action Received for Chinese Patent Application No. 200680044698.0, dated Nov. 4, 2010, 26 pages.
U.S. Appl. No. 60/449,762, filed Feb. 24, 2003, 28 pages.
ACM Digital Library Record, "Autonomous Robots", Downloaded from <http://dl.acm.org/citation.cfm?id=591550ANDpicked=proxANDcfid=360891374ANDcftoken=35225929>, vol. 11, Issue 1, Jul. 2001, 2 pages.
Activemedia, Inc., "Saphira Software Manual", Saphira Version 5.3, ActiveMedia, Inc., 1997, 105 pages.
Activmedia Robotics, "Pioneer 2/PeopleBot TM", Operations Manual, Version 9, Oct. 2001, 78 pages.
Adams, Chris, "Simulation of Adaptive Behavior (SAB'02)", Mobile Robotics Research Group, The Seventh International Conference, retrieved on Jan. 22, 2014, available at: http://www.dai.ed.ac.uk/groups/mrg/MRG.html, Aug. 4-11, 2002, 1 page.
Ando et al., "A Multimedia Self-service Terminal with Conferencing Functions", Robot and Human Communication, RO-MAN'95, Tokyo, Proceedings of 4th IEEE International Workshop, Jul. 5-7, 1995, pp. 357-362.
Android Amusement Corp., "What Marketing Secret Renting Robots from Android Amusement Corp!", (Advertisement), 1982, 1 page.
Apple Inc., "I Phone", iPhone Series, XP002696350, Sep. 21, 2012, pp. 1-29.
Applebome, Peter, "Planning Domesticated Robots for Tomorrow's Household", New York Times, Online available at <http://www.theoldrobots.com/images17/dc17.JPG>, Mar. 4, 1982, pp. 21 and 23.

Bar-Cohen et al., "Virtual Reality Robotic Telesurgery Simulations Using MEMICA Haptic System", Proceedings of SPIE's 8th Annual International Symposium on Smart Structures and Materials, Mar. 5-8, 2001, pp. 1-7.
Barrett, Rick, "Video Conferencing Business Soars as Companies Cut Travel, Some Travel Cuts Are Permanent", http://www.ivci.com/international_video_conferencing_news_videoconferencing_news_19.html, May 13, 2002, 2 pages.
Bartholomew, "Pharmacy Apothecary", available online at <http://classes.bnf.fr/ema/grands/034.htm>, retrieved on Jul. 26, 2012, 2 pages.
Bauer et al., "Remote Telesurgical Mentoring: Feasibility and Efficacy", IEEE, Proceedings of the 33rd Hawaii International Conference on System Sciences, 2000, pp. 1-9.
Bauer, Jeffrey C., "Service Robots in Health Care: The Evolution of Mechanical Solutions to Human Resource Problems", Bon Secours Health System Inc., Technology Early Warning System(TEWS), Future of Service Robots in Health Care, Jun. 2003, pp. 1-10.
Bischoff, Rainer, "Design Concept and Realization of the Humanoid Service Robot HERMES", Field and Service Robotics, Springer, 1998, pp. 485-492.
Blackwell, Gerry, "Video: A Wireless LAN Killer App?", Availabel online at <http://www.wi-fiplanet.com/columns/article.php/1010261/Video-A-Wireless-LAN-Killer>, Retrieved on Nov. 22, 2010, Apr. 16, 2002, 4 pages.
Blaer et al., "TopBot: Automated Network Topology Detection With a Mobile Robot", IEEE, Proceedings of the 2003 International Conference on Robotics 7 Automation, Taipei, Taiwan, Sep. 14-19, 2003, pp. 1582-1587.
Bradner, S., "The Internet Standards Process—Revision 3", Network Working Group, Request for Comments: 2026, BCP: 9, Obsoletes: 1602, Category: Best Current Practice, Oct. 1996, pp. 1-36.
Brenner, Pablo, "A technical tutorial on the IEEE 802.11 protocol", BreezeCOM Wireless Communications, 1997, pp. 1-24.
Breslow et al., "Effect of a Multiple-Site Intensive Care Unit Telemedicine Program on Clinical and Economic Outcome an Alternative Paradigm for Intensivist Staffing", Critical Care Med, vol. 32, No. 1, Jan. 2004, pp. 31-38.
Brooks, Rodney, "A Robust Layered Control System for a Mobile Robot", IEEE, Journal of Robotics and Automation, vol. 2, No. 1, Mar. 1986, pp. 14-23.
Brooks, Rodney Allen, "Remote Presence", Abstracts from Flesh and Machines, How Robots Will Change Us, Feb. 2002, pp. 131-147.
Celi et al., "The eICU: It's Not Just Telemedicine", Critical Care Medicine vol. 29, No. 8 (Supplement), Aug. 2001, pp. 183-189.
Cheetham et al., "Interface Development for a Child's Video Conferencing Robot", Available online at <www.ryerson.ca/pebbles/publications/paper-iea200hfes-last.pdf>, 2000, 4 pages.
Christensen et al., "BeeSoft User's Guide and Reference", Robots for the Real World™, Real World Interface, Inc ., Sep. 26, 1997, 203 pages.
Chu et al., "Detection of Target Mobile Signal Strength", Technical Development, Motorola Inc, Jan. 1999, pp. 205-206.
Jouppi et al., "BiReality: Mutually-Immersive Telepresence", Multimedia '04, Proceedings of the 12th Annual ACM International Conference on Multimedia, Oct. 10-16, 2004, pp. 860-867.
Jouppi et al., "First Steps Towards Mutually-Immersive Mobile Telepresence", CSCW '02, Proceedings of the 2002 ACM conference on Computer Supported Cooperative Work, Nov. 16-20, 2002, pp. 354-363.
Kanehiro et al., "Virtual Humanoid Robot Platform to Develop Controllers of Real Humanoid Robots without Porting", Intelligent Robots and Systems, Proceedings of 2001 IEEE/RSJ International Conference, vol. 2, 2001, pp. 1093-1099.
Kaplan et al., "An Internet Accessible Telepresence", Multimedia Systems Journal, vol. 5, 1996, 7 pages.
Keller et al., "Raven Interface Project", The National Aviary's Teleconferencing Carnegie Mellon University Robot, Interaction and Visual Interface Design, School of Design, Carnegie Mellon University, 2001, 8 pages.

(56) References Cited

OTHER PUBLICATIONS

Khatib, "Robots in Human Environments", Proceedings of International Conference on Control, Automation, Robotics, and Vision ICRACV2000, 1999, 15 pages.

Knight et al., "Active Visual Alignment of a Mobile Stereo Camera Platform", Robotics and Automation, Proceedings of ICRA '00 IEEE International Conference, vol. 4, Apr. 24-28, 2000, pp. 3203-3208.

Koenen, Rob, "MPEG-4: a Powerful Standard for Use in Web and Television Environments", (KPN Research), available online at <http://www.w3.org/Architecture/1998/06/Workshop/paper26>, Jul. 1, 1998, 4 pages.

Kurlowicz et al., "The Mini Mental State Examination (MMSE)", Try This: Best Practices in Nursing Care to Older Adults, A series from the Hartford Institute of Geriatric Nursing, Issue No. 3, Jan. 1999, 2 pages.

Kuzuoka, et al., "Can The GestureCam Be a Surrogate?", Proceedings of the Fourth European Conference on Computer-Supported Cooperative Work, 1995, pp. 181-196.

Lane, Earl, "Automated Aides", Available online at <http://www.cs.cum.edu/nursebot/web/press/nd4380.htm>, Retrieved on Nov. 23, 2010, Oct. 17, 2000, 4 pages.

Lee et al., "A Novel Method of Surgical Instruction: International Telementoring", World Journal of Urology, vol. 16, No. 6, Dec. 1998, pp. 367-370.

Leifer et al., "VIPRR: A Virtually in Person Rehabilitation Robot", Proceedings of 1997 International Conference on Rehabilitation Robotics, Apr. 14-15, 1997, 4 pages.

Lemaire, Edward, "Using Communication Technology to Enhance Rehabilitation Services: A Solution Oriented User Manual", Institute for Rehabilitation Research and Development, Terry Fox Mobile Clinic, The Rehabilitation Centre, Ottawa, Ontario, Canada, Version 2.0, Online available at <http://www.irrd.ca/telehealth/distfile/distman_v2_1.pdf>, 1998-2001, 104 pages.

Library of Congress, "008—Fixed-Length Data Elements (NR)", MARC 21 Format for Classification Data, downloaded from <http://www.loc.gov/marc/classification/cd008.html>, Jan. 2000, pp. 1-14.

Lim et al., "Control to Realize Human-Like Walking of a Biped Humanoid Robot", Systems, Man, and Cybernetics, 2000, IEEE International Conference, vol. 5, 2000, pp. 3271-3276.

Linebarger et al., "Concurrency Control Mechanisms for Closely Coupled Collaboration in Multithreaded Virtual Environments", Department of Computer Science and Engineering, Lehigh University, vol. 13, 2004, 40 pages.

Long, "Robot Navigation Technology", Available Online at <http://www.atp.nist.gov/eao/sp950-1/helpmate.htm>, Retrieved on Nov. 23, 2010, Mar. 1999, 3 pages.

Luna, Nancy, "Robot a New Face on Geriatric Care", ocregister.com, Aug. 6, 2003, 3 pages.

Mack, Michael J., "Minimally Invasive and Robotic Surgery", The Journal of the American Medical Association, vol. 285, No. 5, 2001, pp. 568-572.

Mair, G. M., "Telepresence—The Technology and its Economic and Social Implications", Technology and Society, 1997. 'Technology and Society at a Time of Sweeping Change', Proceedings of 1997 International Symposium, Jun. 20-21, 1997, pp. 118-124.

Martin, Anya, "Brighter Days Ahead", Assisted Living Today, vol. 9, Nov./Dec. 2002, pp. 19-22.

McCardle et al., "The Challenge of Utilizing New Technology in Design Education", Loughborough University, IDATER 2000, pp. 122-127.

Meng et al., "E-Service Robot in Home Healthcare", Proceedings of the 2000 IEEE/RSJ, International Conference on Intelligent Robots and Systems, 2000, pp. 832-837.

Metz, Cade, "HP Labs", Available Online at <http://www.pcmag.com/article2/0,2817,1130820,00.asp>, Jul. 1, 2003, 4 pages.

Michaud, Anne, "Introducing "Nursebot"", Available Online at <http://www.cs.cmu.edu/nursebot/web/press/globe 301/index.html>, Retrieved on May 5, 2008, 2001, 4 pages.

Microsoft Corporation, Inc., "Microsoft NetMeeting 3 Features excerpt from Official Microsoft NetMeeting 3.0 Book", Available at <http://technet.microsoft.com/en-us/library/cc723477.aspx>, Retrieved on Jun. 26, 2012, 6 pages.

Minsky, Marvin, "Telepresence", OMNI Magazine, Jun. 1980, 6 pages.

Montemerlo, "Telepresence: Experiments in Next Generation Internet", Available Online at <http://www.ri.cmu.edu/creative/archives.htm>, Retrieved on May 25, 2008, Oct. 20, 1998.

Murphy, "Introduction to A1 Robotics", A Bradford Book, The MIT Press, Cambridge, Massachusetts, London, England, 2000, 487 pages.

Nakajima et al., "A Multimedia Teleteaching System using an Electronic Whiteboard for Two Way Communication of Motion Videos and Chalkboards", Robot and Human Communication, Proceedings of 2nd IEEE International Workshop, 1993, pp. 436-441.

Nakazato et al., "Group-Based Interface for Content-Based Image Retrieval", Proceedings of the Working Conference on Advanced Visual Interfaces, 2002, pp. 187-194.

Nakazato et al., "ImageGrouper: A Group-Oriented User Interface for Content-Based Image Retrieval and Digital Image Arrangement", Journal of Visual Languages and Computing, vol. 14, No. 4, Aug. 2003, pp. 45-46.

NERSC, "Berkeley Lab's RAGE Telepresence Robot Captures RANDD100 Award", Available at <https://www.nersc.gov/news-publications/news/nersc-center-news/2002/berkeley-lab-s-rage-telepresence-robot-captures-r-and-d100-award/>, Retrieved on Jan. 22, 2014, Jul. 2, 2002, 2 pages.

Nomadic Technologies Inc., "Nomad XR4000 Hardware Manual", Release 1.0, Mar. 1999, 34 pages.

Noritsugu, et al., "Application of Rubber Artificial Muscle Manipulator as a Rehabilitation Robot", Mechatronics, IEEE/ASME Transactions, vol. 2, No. 4, Dec. 1997, pp. 259-267.

North, Michael, "Telemedicine: Sample Script and Specifications for a Demonstration of Simple Medical Diagnosis and Treatment Using Live Two-Way Video on a Computer Network", Greenstar Corporation, 1998, 5 pages.

Ogata et al., "Development of Emotional Communication Robot: WAMOEBA-2R—Experimental evaluation", Proceedings of the 2000 IEEE/RSJ International Conference on Intelligent Robots and Systems, vol. 1, 2000, pp. 175-180.

Ogata et al., "Emotional Communication Robot: WAMOEBA-2R—Emotion Model and Evaluation Experiments", Proceedings of the International Conference on Humanoid Robots, 2000, pp. 1-16.

Oh et al., "Autonomous Battery Recharging for Indoor Mobile Robots", Proceedings of Australian Conference on Robotics and Automation, 2000, pp. 1-6.

Ojha, Anand K., "An application of Virtual Reality in Rehabilitation", Proceedings of the 1994 IEEE Southeastcon 94. Creative Technology Transfer—A Global Affair, Apr. 1994, pp. 4-6.

Osborn, Jim, "Quality of Life Technology Center", QoLT Research Overview:A National Science Foundation Engineering Research Center, Carnegie Mellon University of Pittsburgh, 2 pages.

Panusopone et al., "Performance Comparison of MPEG-4 and H.263+ for Streaming Video Applications", Circuits Systems Signal Processing, vol. 20, No. 3, 2001, pp. 293-309.

Paulos et al., "A World Wide Web Telerobotic Remote Environment Browser", Available at <http://www.w3.org/Conferences/WWW4/Papers/326/>, Retrieved on Nov. 23, 2010, 1995, 15 pages.

Paulos et al., "Designing Personal Tele-Embodiment", Proceedings of IEEE International Conference on Robotics and Automation, vol. 4, May 16-20, 1998, pp. 3173-3178.

Paulos, Eric J., "Personal Tele-Embodiment", Dissertation, Doctor of Philosophy in Computer Science in the Graduate Division of the University of California at Berkeley, 2001, 282 pages.

Paulos, Eric John, "Personal Tele-Embodiment", OskiCat Catalog Record, UCB Library Catalog, 2001, 3 pages.

Paulos, Eric John, "Personal Tele-Embodiment", Introductory and cover pages from 2001 Dissertation including Contents table, together with e-mails relating thereto from UC Berkeley Libraries, as shelved at UC Berkeley Engineering Library (Northern Regional library Facility), May 8, 2002, 25 pages (including 4 pages of e-mails).

(56) References Cited

OTHER PUBLICATIONS

Paulos et al., "Personal Tele-Embodiment", Chapter 9 in Goldberg et al., ed. "Beyond webcams", MIT Press, Jan. 4, 2002, pp. 155-167.
Paulos et al., "PRoP: Personal Roving Presence", ACM:CHI Proceedings of CHI '98, 1998, 8 pages.

* cited by examiner

MULTI-CAMERA MOBILE TELECONFERENCING PLATFORM

BACKGROUND OF THE INVENTION

1. Field of the Invention

The subject matter disclosed generally relates to the field of mobile two-way teleconferencing.

2. Background Information

Robots have been used in a variety of applications ranging from remote control of hazardous material to assisting in the performance of surgery. For example, U.S. Pat. No. 5,762,458 issued to Wang et al. discloses a system that allows a surgeon to perform minimally invasive medical procedures through the use of robotically controlled instruments. One of the robotic arms in the Wang system moves an endoscope that has a camera. The camera allows a surgeon to view a surgical area of a patient.

Tele-robots such as hazardous waste handlers and bomb detectors may contain a camera that allows the operator to view the remote site. Canadian Pat. No. 2289697 issued to Treviranus, et al. discloses a teleconferencing platform that has both a camera and a monitor. The platform includes mechanisms to both pivot and raise the camera and the monitor. The Treviranus patent also discloses embodiments with a mobile platform, and different mechanisms to move the camera and the monitor.

There has been marketed a mobile robot introduced by InTouch Technologies, Inc., the assignee of this application, under the trademarks COMPANION and RP-6. The InTouch robot is controlled by a user at a remote station. The remote station may be a personal computer with a joystick that allows the user to remotely control the movement of the robot. Both the robot and remote station have cameras, monitors, speakers and microphones to allow for two-way video/audio communication. The robot camera provides video images to a screen at the remote station so that the user can view the robot's surroundings and move the robot accordingly.

When moving the robot it is desirable to have a relatively wide view angle so that the user is provided with an optimal view of the robot's surroundings. It is also desirable to provide the robot with a zoom lens function so that the user can obtain a closer view of an image. It would be desirable to provide an interface for a remote controlled robot system that allows a user to easily switch between zoom and non-zoom images. It would also be desirable to provide memory functions so that the user can return to certain camera positions.

BRIEF SUMMARY OF THE INVENTION

A remote controlled robot system that includes a mobile robot and a remote control station. The mobile robot moves in response to robot control commands transmitted by the remote control station. The remote control station includes a monitor that displays a robot view field. The remote control station has a graphical user function that allows the robot view field to display either a zoom image or a non-zoom image provided by the mobile robot.

DETAILED DESCRIPTION

Disclosed is a remote controlled robot system that includes a mobile robot and a remote control station. A user can control movement of the robot from the remote control station. The mobile robot includes a camera system that can capture and transmit to the remote station a zoom image and a non-zoom image. The remote control station includes a monitor that displays a robot view field. The robot view field can display the non-zoom image. The zoom image can be displayed in the robot view field by highlighting an area of the non-zoom field. The remote control station may also store camera positions that allow a user to move the camera system to preset positions.

Figure 1:
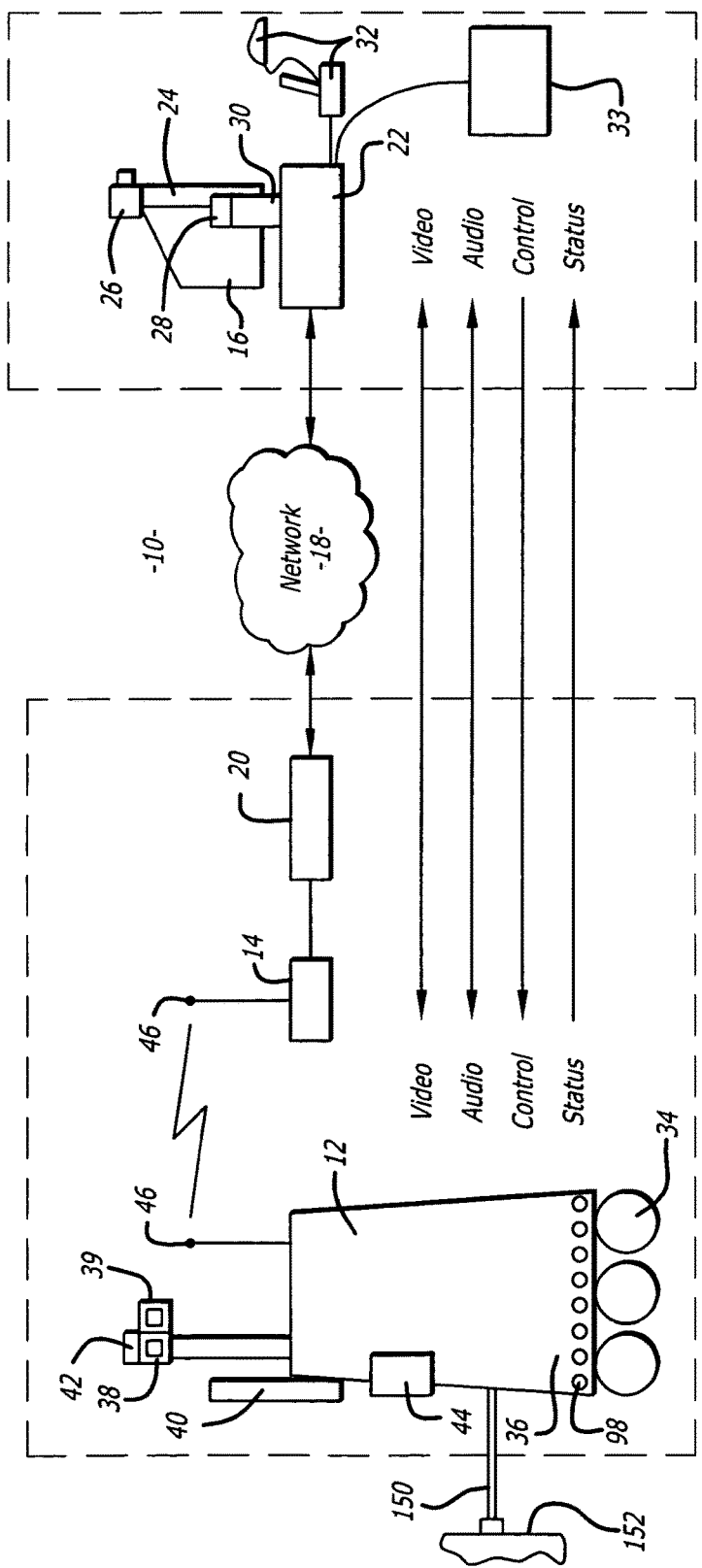
FIG. 1 is an illustration of a robotic system.

Referring to the drawings more particularly by reference numbers, FIG. 1 shows a robotic system 10 that can be used to conduct a remote visit. The robotic system 10 includes a robot 12, a base station 14 and a remote control station 16. The remote control station 16 may be coupled to the base station 14 through a network 18. By way of example, the network 18 may be either a packet switched network such as the Internet, or a circuit switched network such has a Public Switched Telephone Network (PSTN) or other broadband system. The base station 14 may be coupled to the network 18 by a modem 20 or other broadband network interface device. By way of example, the base station 14 may be a wireless router. Alternatively, the robot 12 may have a direct connection to the network thru for example a satellite.

The remote control station 16 may include a computer 22 that has a monitor 24, a camera 26, a microphone 28 and a speaker 30. The computer 22 may also contain an input device 32 such as a joystick and/or a mouse and a keyboard 33. The control station 16 is typically located in a place that is remote from the robot 12. Although only one remote control station 16 is shown, the system 10 may include a plurality of remote stations. In general any number of robots 12 may be controlled by any number of remote stations 16 or other robots 12. For example, one remote station 16 may be coupled to a plurality of robots 12, or one robot 12 may be coupled to a plurality of remote stations 16, or a plurality of robots 12.

Each robot 12 includes a movement platform 34 that is attached to a robot housing 36. Also attached to the robot housing 36 is a pair of cameras 38 and 39, a monitor 40, a microphone(s) 42 and a speaker(s) 44. The microphone 42 and speaker 30 may create a stereophonic sound. The robot 12 may also have an antenna 46 that is wirelessly coupled to an antenna 48 of the base station 14. The system 10 allows a user at the remote control station 16 to move the robot 12 through operation of the input device 32. The robot cameras 38 and 39 are coupled to the remote monitor 24 so that a user at the remote station 16 can view a patient. Likewise, the robot monitor 40 is coupled to, the remote camera 26 so that the patient can view the user. The microphones 28 and 42, and speakers 30 and 44, allow for audible communication between the patient and the user.

Camera 38 may provide a wide angle view. Conversely, camera 39 may contain a zoom lens to provide a narrow angle view. Camera 39 can capture a zoom image that is transmitted to the remote control station. Camera 38 can capture a non-zoom image that can be transmitted to the remote control station. Although two cameras are shown and described, it is to be understood that the robot may contain only one camera that has the capability to provide a zoom image and a non-zoom image.

The remote station computer 22 may operate Microsoft OS software and WINDOWS XP or other operating systems such as LINUX. The remote computer 22 may also operate a video driver, a camera driver, an audio driver and a joystick driver. The video images may be transmitted and received with compression software such as MPEG CODEC.

Figure 2:
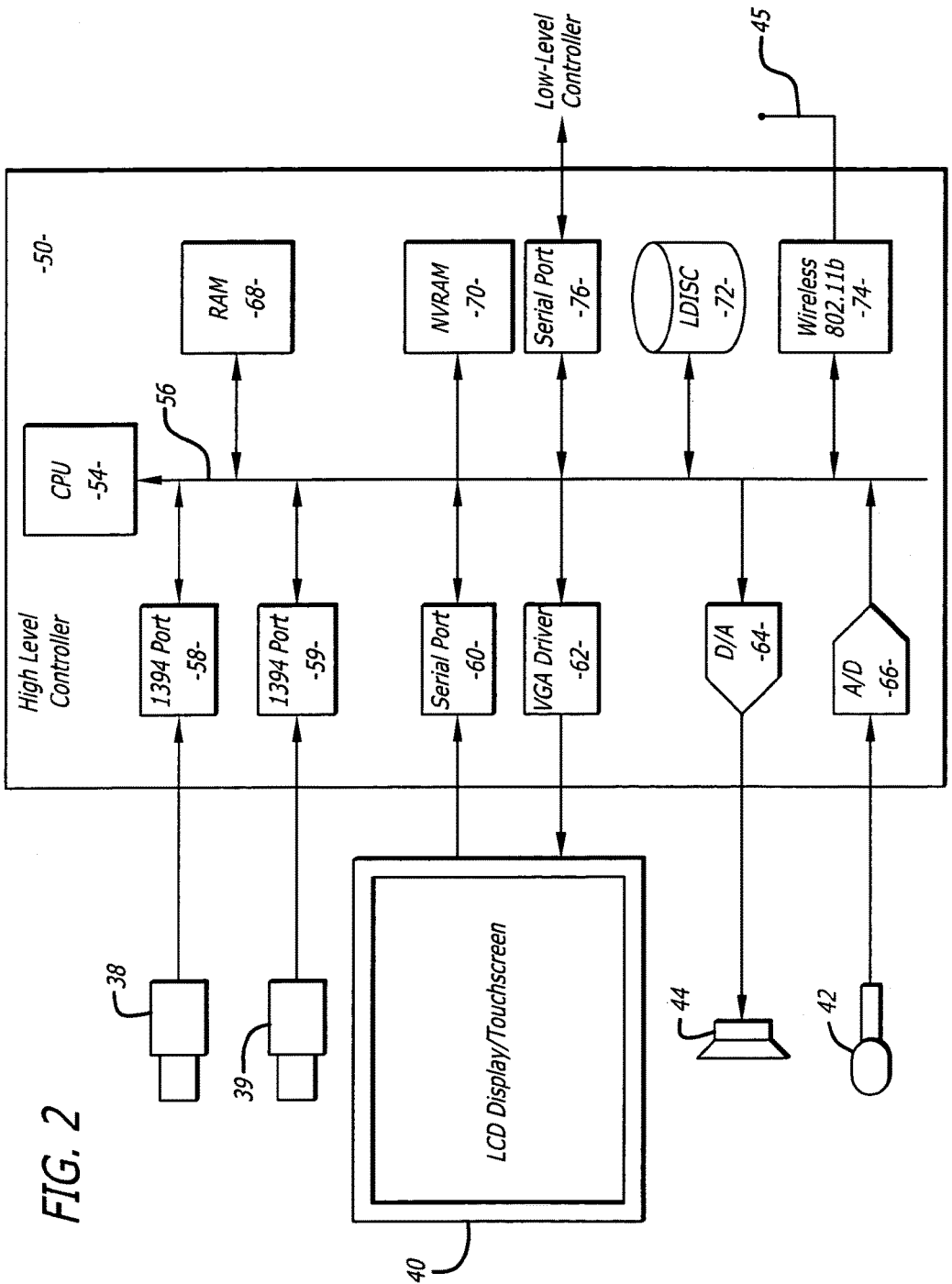
FIG. 2 is a schematic of an electrical system of a robot.
Figure 3:
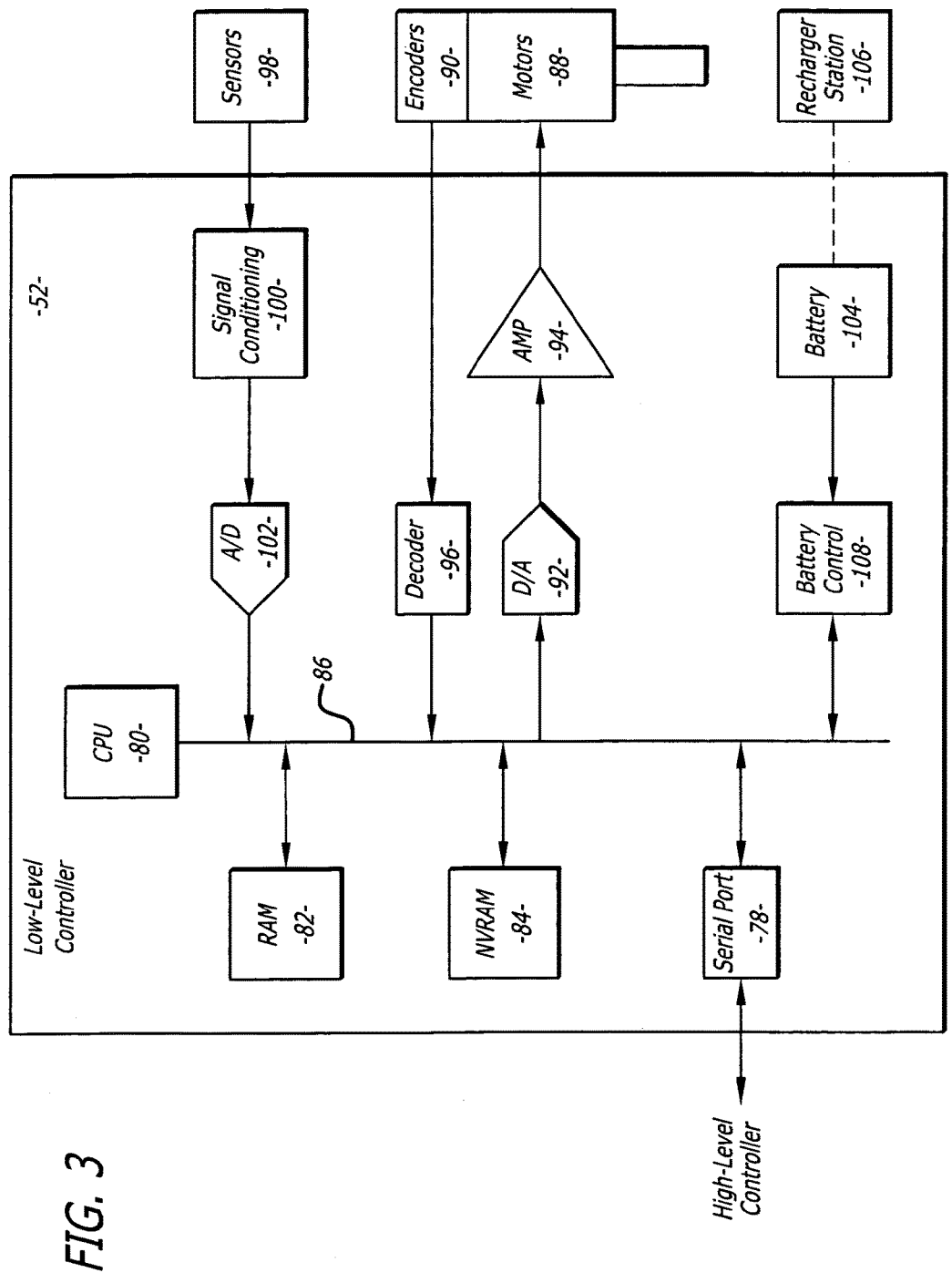
FIG. 3 is a further schematic of the electrical system of the robot.

FIGS. 2 and 3 show an embodiment of a robot 12. Each robot 12 may include a high level control system 50 and a low level control system 52. The high level control system 50 may include a processor 54 that is connected to a bus 56. The bus 56 is coupled to the cameras 38 and 39 by an input/output (I/O) ports 58 and 59, respectively. The monitor 40 is coupled to the bus 56 by a serial output port 60 and a VGA driver 62. The monitor 40 may include a touchscreen function that allows the patient to enter input by touching the monitor screen.

The speaker 44 is coupled to the bus 56 by a digital to analog converter 64. The microphone 42 is coupled to the bus 56 by an analog to digital converter 66. The high level controller 50 may also contain random access memory (RAM) device 68, a non-volatile RAM device 70 and a mass storage device 72 that are all coupled to the bus 62. The mass storage device 72 may contain medical files of the patient that can be accessed by the user at the remote control station 16. For example, the mass storage device 72 may contain a picture of the patient. The user, particularly a health care provider, can recall the old picture and make a side by side comparison on the monitor 24 with a present video image of the patient provided by the camera 38. The robot antennae 45 may be coupled to a wireless transceiver 74. By way of example, the transceiver 74 may transmit and receive information in accordance with IEEE 802.11b.

The controller 54 may operate with a LINUX OS operating system. The controller 54 may also operate MS WINDOWS along with video, camera and audio drivers for communication with the remote control station 16. Video information may be transceived using MPEG CODEC compression techniques. The software may allow the user to send e-mail to the patient and vice versa, or allow the patient to access the Internet. In general the high level controller 50 operates to control communication between the robot 12 and the remote control station 16.

The remote control station 16 may include a computer that is similar to the high level controller 50. The computer would have a processor, memory, I/O, software, firmware, etc. for generating, transmitting, receiving and processing information.

The high level controller 50 may be linked to the low level controller 52 by serial ports 76 and 78. The low level controller 52 includes a processor 80 that is coupled to a RAM device 82 and non-volatile RAM device 84 by a bus 86. Each robot 12 contains a plurality of motors 88 and motor encoders 90. The motors 88 can actuate the movement platform and move other parts of the robot such as the monitor and camera. The encoders 90 provide feedback information regarding the output of the motors 88. The motors 88 can be coupled to the bus 86 by a digital to analog converter 92 and a driver amplifier 94. The encoders 90 can be coupled to the bus 86 by a decoder 96. Each robot 12 also has a number of proximity sensors 98 (see also FIG. 1). The position sensors 98 can be coupled to the bus 86 by a signal conditioning circuit 100 and an analog to digital converter 102.

The low level controller 52 runs software routines that mechanically actuate the robot 12. For example, the low level controller 52 provides instructions to actuate the movement platform to move the robot 12. The low level controller 52 may receive movement instructions from the high level controller 50. The movement instructions may be received as movement commands from the remote control station or another robot. Although two controllers are shown, it is to be understood that each robot 12 may have one controller, or more than two controllers, controlling the high and low level functions.

The various electrical devices of each robot 12 may be powered by a battery(ies) 104. The battery 104 may be recharged by a battery recharger station 106 (see also FIG. 1). The low level controller 52 may include a battery control circuit 108 that senses the power level of the battery 104. The low level controller 52 can sense when the power falls below a threshold and then send a message to the high level controller 50.

The system may be the same or similar to a robotic system provided by the assignee InTouch-Health, Inc. of Santa Barbara, Calif. under the name RP-6. The system may also be the same or similar to the system disclosed in application Ser. No. 10/206,457 published on Jan. 29, 2004, which is hereby incorporated by reference.

Figure 4:
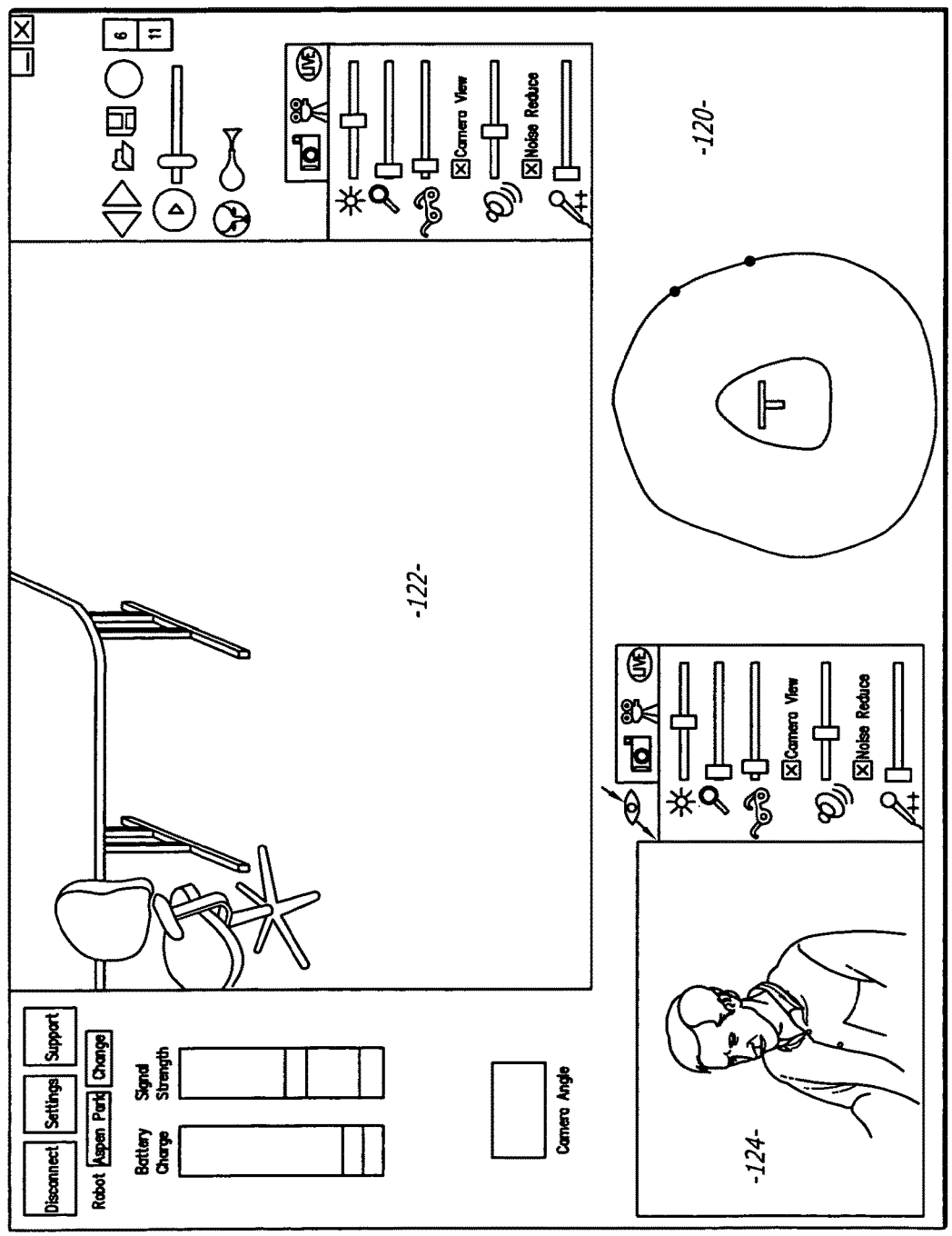
FIG. 4 is a graphical user interface of a remote station.

FIG. 4 shows a display user interface ("DUI") 120 that can be displayed at the remote station 16. The DUI 120 may include a robot view field 122 that displays a video image provided by the camera of the robot. The DUI 120 may also include a station view field 124 that displays a video image provided by the camera of the remote station 16. The DUI 120 may be part of an application program stored and operated by the computer 22 of the remote station 16.

Figure 5:
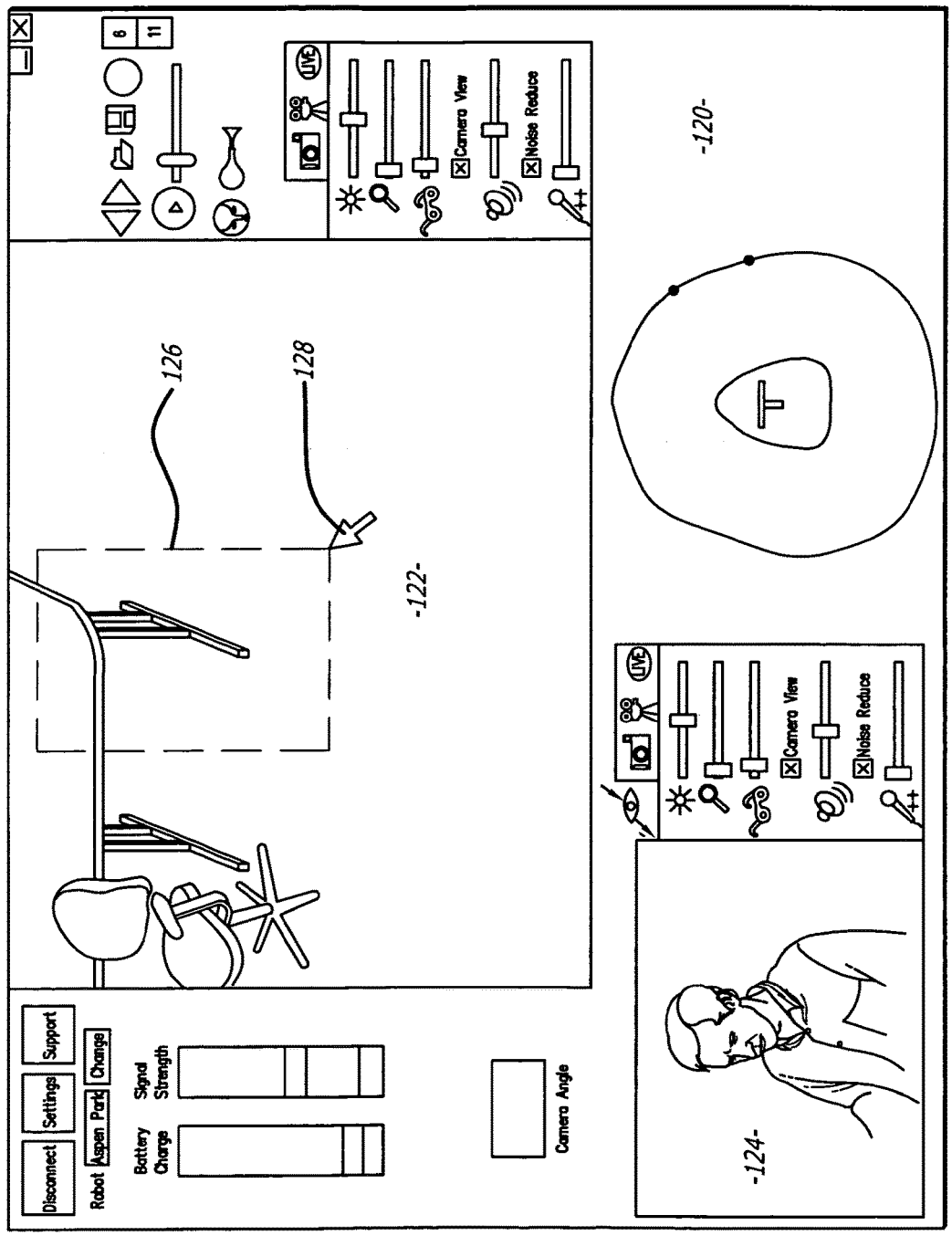
FIG. 5 is similar to FIG. 4 showing a portion of a non-zoom image highlighted.
Figure 6:
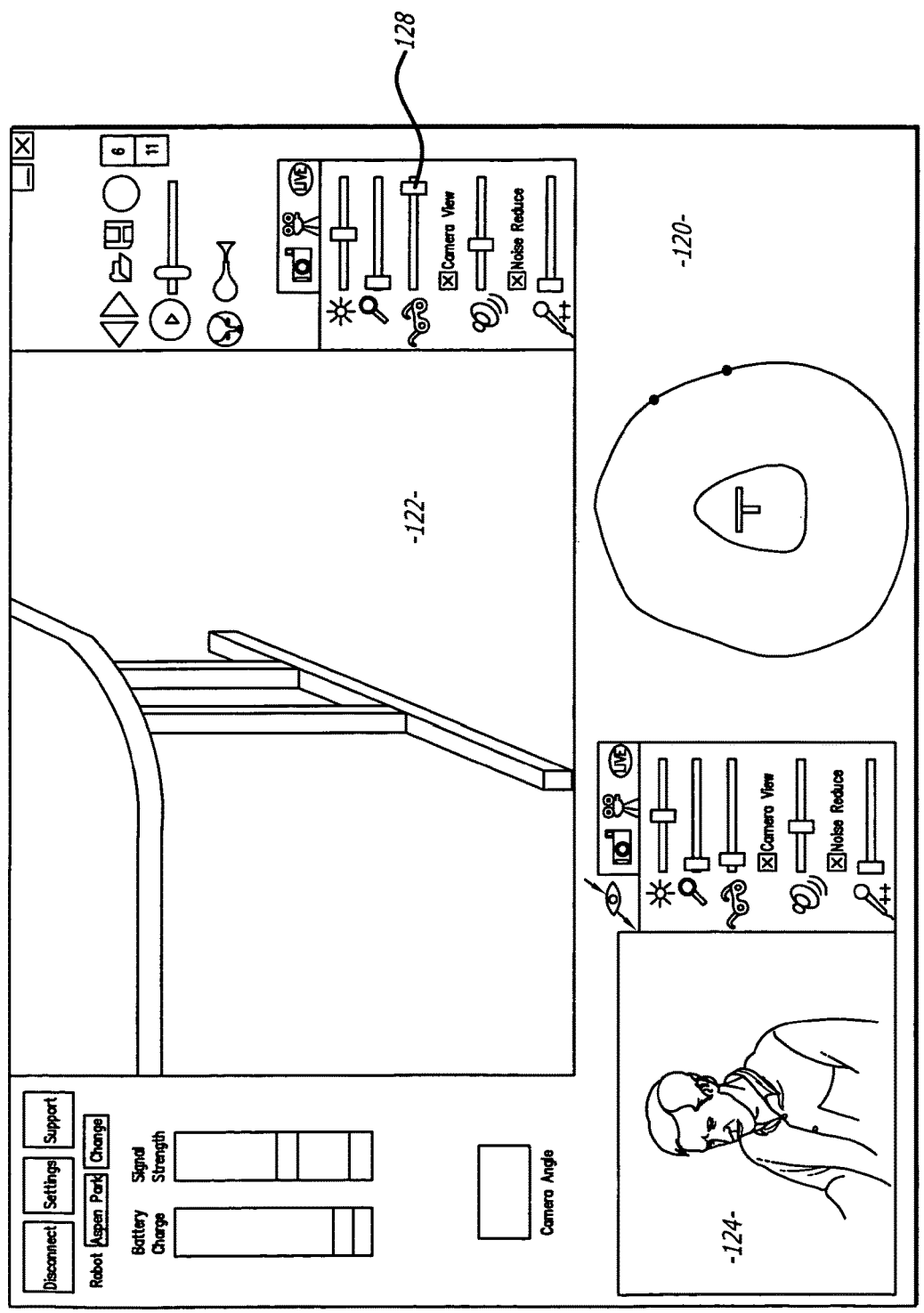
FIG. 6 is similar to FIG. 4 showing a zoom image being displayed by a robot view field.

The robot view field 122 may display a non-zoom image provided by the camera system of the robot. As shown by FIGS. 5 and 6, the user can highlight a portion of the non-zoom image to display a zoom image that corresponds to the highlighted area 126. By way of example, the highlighted area 126 can be initiated by left-clicking a mouse. The user can then drag the cursor 128, while holding down the left-click, to create the highlighted area 126. When the user releases the left-click, the remote station transmits commands to move the robot camera to point at the center of the highlighted area 126 and provide the zoom image corresponding to the area. Alternatively, the user can click on the mouse and a zoom area centered about the cursor will be displayed. The user can switch back to the non-zoom image by manipulating graphical icon 128 to move the slide bar to a far left position. This feature allows a user to readily switch between zoom and non-zoom images provided by the robot camera system. Thus a user can utilize the non-zoom image while moving the robot, and the zoom image feature to take a closer look at people or objects in the field of view.

Figure 7:
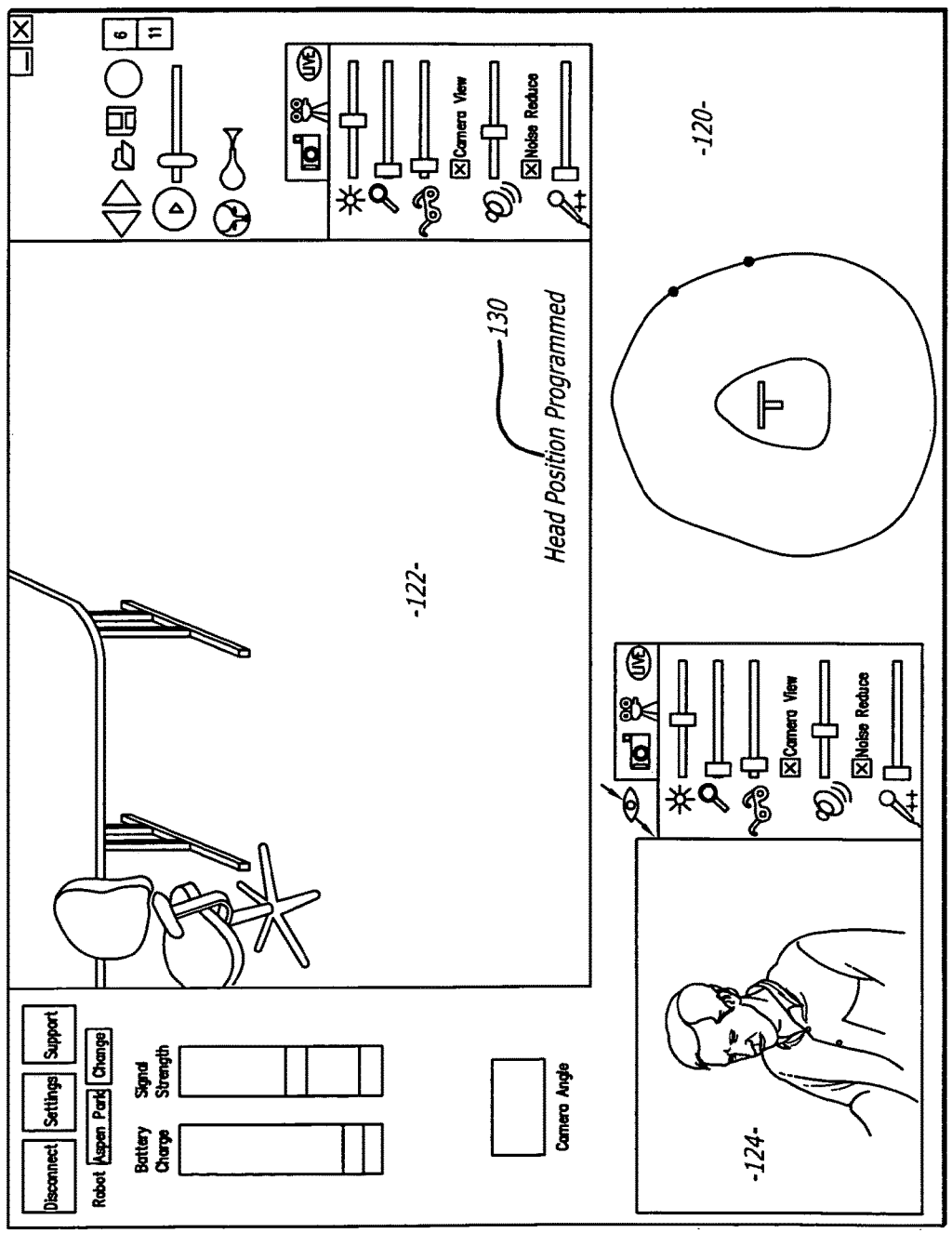
FIG. 7 is similar to FIG. 4 showing a message that indicates a camera position has been stored.

The remote control station can store camera positions so that the user can readily go to a desired camera position. By way of example, a camera location can be stored by depressing a key on the keyboard. The F4 key may be depressed to store a camera position. As shown in FIG. 7 a visual indication 130 may be displayed to indicate to the user that the camera position has been stored. Subsequently pressing the key will cause the remote station to transmit a command(s) to move the robot camera system to the desired position. Other keys such as F5 through F12 can be used to create 9 potential stored camera locations. A new camera position can be stored by pressing and holding down one of the keys F4-F12.

The mouse 32 can be used to move the cameras of the robot. Movement of the mouse 32 may cause a corresponding movement of the cameras. The scale between the mouse and the camera movements may be varied by the user. Movement of the mouse may also cause the system to display zoom and non-zoom images.

In operation, the robot 12 may be placed in a home or a facility where one or more patients are to be monitored and/or assisted. The facility may be a hospital or a residential care facility. By way of example, the robot 12 may be placed in a home where a health care provider may monitor and/or assist the patient. Likewise, a friend or family member may communicate with the patient. The cameras and monitors at both the robot and remote control stations allow for teleconferencing between the patient and the person at the remote station(s).

The robot 12 can be maneuvered through the home or a facility by manipulating the input device 32 at a remote station 16. The robot 10 may be controlled by a number of different users. To accommodate for this the robot may have an arbitration system. The arbitration system may be integrated into the operating system of the robot 12. For example, the arbitration technique may be embedded into the operating system of the high-level controller 50.

By way of example, the users may be divided into classes that include the robot itself, a local user, a caregiver, a doctor, a family member, or a service provider. The robot 12 may override input commands that conflict with robot operation. For example, if the robot runs into a wall, the system may ignore all additional commands to continue in the direction of the wall. A local user is a person who is physically present with the robot. The robot could have an input device that allows local operation. For example, the robot may incorporate a voice recognition system that receives and interprets audible commands.

A caregiver is someone who remotely monitors the patient. A doctor is a medical professional who can remotely control the robot and also access medical files contained in the robot memory. The family and service users remotely access the robot. The service user may service the system such as by upgrading software, or setting operational parameters.

The robot 12 may operate in one of two different modes; an exclusive mode, or a sharing mode. In the exclusive mode only one user has access control of the robot. The exclusive mode may have a priority assigned to each type of user. By way of example, the priority may be in order of local, doctor, caregiver, family and then service user. In the sharing mode two or more users may share access with the robot. For example, a caregiver may have access to the robot, the caregiver may then enter the sharing mode to allow a doctor to also access the robot. Both the caregiver and the doctor can conduct a simultaneous tele-conference with the patient.

The arbitration scheme may have one of four mechanisms; notification, timeouts, queue and call back. The notification mechanism may inform either a present user or a requesting user that another user has, or wants, access to the robot. The timeout mechanism gives certain types of users a prescribed amount of time to finish access to the robot. The queue mechanism is an orderly waiting list for access to the robot. The call back mechanism informs a user that the robot can be accessed. By way of example, a family user may receive an e-mail message that the robot is free for usage. Tables I and II, show how the mechanisms resolve access request from the various users.

TABLE I

| User | Access Control | Medical Record | Command Override | Software/Debug Access | Set Priority |
|---|---|---|---|---|---|
| Robot | No | No | Yes (1) | No | No |
| Local | No | No | Yes (2) | No | No |
| Caregiver | Yes | Yes | Yes (3) | No | No |
| Doctor | No | Yes | No | No | No |
| Family | No | No | No | No | No |
| Service | Yes | No | Yes | Yes | Yes |

TABLE II

| | | Requesting User | | | | |
|---|---|---|---|---|---|---|
| | | Local | Caregiver | Doctor | Family | Service |
| Current User | Local | Not Allowed | Warn current user of pending user<br>Notify requesting user that system is in use<br>Set timeout | Warn current user of pending user<br>Notify requesting user that system is in use<br>Set timeout = 5 m | Warn current user of pending user<br>Notify requesting user that system is in use<br>Set timeout = 5 m<br>Call back | Warn current user of pending user<br>Notify requesting user that system is in use<br>No timeout<br>Call back |
| | Caregiver | Warn current user of pending user.<br>Notify requesting user that system is in use.<br>Release control | Not Allowed | Warn current user of pending user<br>Notify requesting user that system is in use<br>Set timeout = 5 m<br>Queue or callback | Warn current user of pending user<br>Notify requesting user that system is in use<br>Set timeout = 5 m | Warn current user of pending user<br>Notify requesting user that system is in use<br>No timeout<br>Callback |
| | Doctor | Warn current user of pending user<br>Notify requesting user that system is in use<br>Release control | Warn current user of pending user<br>Notify requesting user that system is in use<br>Set timeout = 5 m | Warn current user of pending user<br>Notify requesting user that system is in use<br>No timeout<br>Callback | Notify requesting user that system is in use<br>No timeout<br>Queue or callback | Warn current user of pending user<br>Notify requesting user that system is in use<br>No timeout<br>Callback |
| | Family | Warn current user of pending user<br>Notify requesting user that system is | Notify requesting user that system is in use<br>No timeout | Warn current user of pending user<br>Notify requesting user that system is in use | Warn current user of pending user<br>Notify requesting user that system is in use | Warn current user of pending user<br>Notify requesting user that system is in |

TABLE II-continued

| | Requesting User | | | | |
|---|---|---|---|---|---|
| | Local | Caregiver | Doctor | Family | Service |
| | in use<br>Release Control | Put in queue or callback | Set timeout = 1 m | Set timeout = 5 m<br>Queue or callback | use<br>No timeout<br>Callback |
| Service | Warn current user of pending user<br>Notify requesting user that system is in use<br>No timeout | Notify requesting user that system is in use<br>No timeout<br>Callback | Warn current user of request<br>Notify requesting user that system is in use<br>No timeout<br>Callback | Warn current user of pending user<br>Notify requesting user that system is in use<br>No timeout<br>Queue or callback | Not Allowed |

The information transmitted between the station 16 and the robot 12 may be encrypted. Additionally, the user may have to enter a password to enter the system 10. A selected robot is then given an electronic key by the station 16. The robot 12 validates the key and returns another key to the station 16. The keys are used to encrypt information transmitted in the session.

The robot 12 and remote station 16 transmit commands through the broadband network 18. The commands can be generated by the user in a variety of ways. For example, commands to move the robot may be generated by moving the joystick 32 (see FIG. 1). The commands are preferably assembled into packets in accordance with TCP/IP protocol. Table III provides a list of control commands that are generated at the remote station and transmitted to the robot through the network.

TABLE III

| Control Commands | | |
|---|---|---|
| Command | Example | Description |
| drive | drive 10.0 0.0 5.0 | The drive command directs the robot to move at the specified velocity (in cm/sec) in the (x, y) plane, and turn its facing at the specified rate (degrees/sec). |
| goodbye | goodbye | The goodbye command terminates a user session and relinquishes control of the robot |
| gotoHomePosition | gotoHomePosition 1 | The gotoHomePosition command moves the head to a fixed "home" position (pan and tilt), and restores zoom to default value. The index value can be 0, 1, or 2. The exact pan/tilt values for each index are specified in robot configuration files. |
| head | head vel pan 5.0 tilt 10.0 | The head command controls the head motion. It can send commands in two modes, identified by keyword: either positional ("pos") or velocity ("vol"). In velocity mode, the pan and tilt values are desired velocities of the head on the pan and tilt axes, in degree/sec. A single command can include just the pan section, or just the tilt section, or both. |
| keepalive | keepalive | The keepalive command causes no action, but keeps the communication (socket) link open so that a session can continue. In scripts, it can be used to introduce delay time into the action. |
| odometry | odometry 5 | The odometry command enables the flow of odometry messages from the robot. The argument is the number of times odometry is to be reported each second. A value of 0 turns odometry off. |
| reboot | reboot | The reboot command causes the robot computer to reboot immediately. The ongoing session is immediately broken off. |
| restoreHeadPosition | restoreHeadPosition | The restoreHeadPosition functions like the gotoHomePosition command, but it homes the head to a position previously saved with gotoHomePosition. |
| saveHeadPosition | saveHeadPosition | The saveHeadPosition command causes the robot to save the current head position (pan and tilt) in a scratch location in temporary storage so that this position can be restored. Subsequent calls to "restoreHeadPosition" will restore this saved position. Each call to |

TABLE III-continued

Control Commands

| Command | Example | Description |
|---|---|---|
| setCameraFocus | setCameraFocus 100.0 | saveHeadPosition overwrites any previously saved position. The setCameraFocus command controls focus for the camera on the robot side. The value sent is passed "raw" to the video application running on the robot, which interprets it according to its own specification. |
| setCameraZoom | setCameraZoom 100.0 | The setCameraZoom command controls zoom for the camera on the robot side. The value sent is passed "raw" to the video application running on the robot, which interprets it according to its own specification. |
| shutdown | Shutdown | The shutdown command shuts down the robot and powers down its computer. |
| stop | stop | The stop command directs the robot to stop moving immediately. It is assumed this will be as sudden a stop as the mechanism can safely accommodate. |
| timing | Timing 3245629 500 | The timing message is used to estimate message latency. It holds the UCT value (seconds + milliseconds) of the time the message was sent, as recorded on the sending machine. To do a valid test, you must compare results in each direction (i.e., sending from machine A to machine B, then from machine B to machine A) in order to account for differences in the clocks between the two machines. The robot records data internally to estimate average and maximum latency over the course of a session, which it prints to log files. |
| userTask | userTask "Jane Doe" "Remote Visit" | The userTask command notifies the robot of the current user and task. It typically is sent once at the start of the session, although it can be sent during a session if the user and/or task change. The robot uses this information for record-keeping. |

Table IV provides a list of reporting commands that are generated by the robot and transmitted to the remote station through the network.

TABLE IV

Reporting Commands

| Command | Example | Description |
|---|---|---|
| abnormalExit | abnormalExit | This message informs the user that the robot software has crashed or otherwise exited abnormally. Te robot software catches top-level exceptions and generates this message if any such exceptions occur. |
| bodyType | bodyType 3 | The bodyType message informs the station which type body (using the numbering of the mechanical team) the current robot has. This allows the robot to be drawn correctly in the station user interface, and allows for any other necessary body-specific adjustments. |
| driveEnabled | driveEnabled true | This message is sent at the start of a session to indicate whether the drive system is operational. |
| emergencyShutdown | emergencyShutdown | This message informs the station that the robot software has detected a possible "runaway" condition (an failure causing the robot to move out of control) and is shutting the entire system down to prevent hazardous motion. |
| odometry | odometry 10 20 340 | The odometry command reports the current (x, y) position (cm) and body orientation |

TABLE IV-continued

Reporting Commands

| Command | Example | Description |
| --- | --- | --- |
| | | (degrees) of the robot, in the original coordinate space of the robot at the start of the session. |
| sensorGroup | group_data | Sensors on the robot are arranged into groups, each group of a single type (bumps, range sensors, charge meter, etc.) The sensorGroup message is sent once per group at the start of each session. It contains the number, type, locations, and any other relevant data for the sensors in that group. The station assumes nothing about the equipment carried on the robot; everything it knows about the sensors comes from the sensorGroup messages. |
| sensorState | groupName state data | The sensorState command reports the current state values for a specified group of sensor. The syntax and interpretation for the state data is specific to each group. This message is sent once for each group at each sensor evaluation (normally several times per second). |
| systemError | systemError driveController | This message informs the station user of a failure in one of the robot's subsystems. The error_type argument indicates which subsystem failed, including driveController, sensorController, headHome. |
| systemInfo | systemInfo wireless 45 | This message allows regular reporting of information that falls outside the sensor system such as wireless signal strength. |
| text | text "This is some text" | The text string sends a text string from the robot to the station, where the string is displayed to the user. This message is used mainly for debugging. |
| version | version 1.6 | This message identifies the software version currently running on the robot. It is sent once at the start of the session to allow the station to do any necessary backward compatibility adjustments. |

The processor 54 of the robot high level controller 50 may operate a program that determines whether the robot 12 has received a robot control command within a time interval. For example, if the robot 12 does not receive a control command within 2 seconds then the processor 54 provides instructions to the low level controller 50 to stop the robot 12. Although a software embodiment is described, it is to be understood that the control command monitoring feature could be implemented with hardware, or a combination of hardware and software. The hardware may include a timer that is reset each time a control command is received and generates, or terminates, a command or signal, to stop the robot.

The remote station computer 22 may monitor the receipt of video images provided by the robot camera. The computer 22 may generate and transmit a STOP command to the robot if the remote station does not receive or transmit an updated video image within a time interval. The STOP command causes the robot to stop. By way of example, the computer 22 may generate a STOP command if the remote control station does not receive a new video image within 2 seconds. Although a software embodiment is described, it is to be understood that the video image monitoring feature could be implemented with hardware, or a combination of hardware and software. The hardware may include a timer that is reset each time a new video image is received and generates, or terminates, a command or signal, to generate the robot STOP command.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A teleconferencing system, comprising:
a teleconferencing device including a housing that supports a monitor and a camera system that includes a first camera and a second camera mounted to the housing such that the first camera and the second camera face substantially the same direction, the first camera having a first field of view and the second camera having a second field of view that is different from the first field of view; and,
a remote station that includes a camera, a monitor, and a graphical user interface function that provides a zoom input, the remote station monitor displays a display user interface including a local view field that displays an image captured by the remote station camera and a remote view field that displays either the image captured by the first camera or the image captured by the second camera, wherein the display user interface switches the remote view field to display either the image captured by the first camera or the image captured by the second camera depending on the zoom input, the remote station monitor displaying only one of the images from the first or second cameras at a time, and wherein the monitor of the teleconferencing device displays the image captured by the remote station camera.

2. The system of claim 1, wherein said graphical user interface function includes specifying a highlighted area within the displayed image.

3. The system of claim 2, wherein specifying the highlighted area is initiated by depressing a mouse.

4. The system of claim 1, wherein said graphical user interface function includes a slide bar.

5. The system of claim 2, wherein said camera system moves to a center of said highlighted area.

6. The system of claim 1, wherein said remote station includes at least one stored camera position.

7. The system of claim 6, wherein said remote station includes a keyboard and said stored camera position is stored by depressing a key on said keyboard.

8. The system of claim 7, wherein said camera system moves in response to said stored camera position in response to said key being depressed.

9. The system of claim 6, wherein said station monitor displays an indication that said stored camera position has been stored.

10. A method for a teleconferencing system including a teleconferencing device that has a housing that supports a monitor and a camera system including a first camera and a second camera mounted to the housing such that the first camera and the second camera face substantially the same direction, the first camera having a first field of view and the second camera having a second field of view that is different from the first field of view, the method comprising:
- displaying an image captured by a camera of a remote station in a local view field of a display user interface displayed on a monitor of the remote station;
- displaying an image captured by the first camera in a remote view field of the display user interface displayed on the remote station monitor;
- switching the remote view field to display an image captured by the second camera in place of the image captured by the first camera in response to a zoom input provided by a user via a graphical user interface function, wherein the remote station monitor displays only one of the images from the first camera or the second camera at a time; and,
- displaying the image captured by the remote station camera on the monitor of the teleconferencing device.

11. The method of claim 10, wherein the image captured by the second camera corresponds to an area specified by highlighting an area within the image captured by the first camera.

12. The method of claim 10, wherein the step of switching the remote view field is responsive to user input received from a mouse.

* * * * *